(12) United States Patent
Beard et al.

(10) Patent No.: US 6,465,647 B1
(45) Date of Patent: Oct. 15, 2002

(54) OXYGEN, SULFUR AND NITROGEN SUBSTITUTED CYCLOHEXENE AND CYCLOHEXANE DERIVATIVES HAVING RETINOID-LIKE BIOLOGICAL ACTIVITY

(75) Inventors: Richard L. Beard; Diana F. Colon, both of Newport Beach; Roshantha A. Chandraratna, Mission Viejo, all of CA (US)

(73) Assignee: Allergan, Inc., Irvine, CA (US)

( * ) Notice: Subject to any disclaimer, the term of this patent is extended or adjusted under 35 U.S.C. 154(b) by 108 days.

(21) Appl. No.: 09/634,727

(22) Filed: Aug. 4, 2000

Related U.S. Application Data

(62) Division of application No. 09/307,061, filed on May 7, 1999, now Pat. No. 6,166,244.

(51) Int. Cl.[7] .................... C07D 237/02; C07D 213/06; C07D 333/18; C07C 333/00; C07C 239/00
(52) U.S. Cl. .................. 544/224; 544/242; 544/336; 546/340; 546/348; 548/204; 548/235; 548/341.5; 548/373.1; 549/78; 549/80; 549/229; 558/234; 558/248; 558/250; 558/257; 558/260; 558/275; 564/74; 564/161; 564/182
(58) Field of Search ................... 544/224, 242, 544/336; 546/340, 348; 548/204, 235, 341.5, 373.1; 549/78, 80, 229; 558/234, 248, 250, 257, 260, 275; 564/74, 161, 182

(56) References Cited

U.S. PATENT DOCUMENTS

| | | | |
|---|---|---|---|
| 4,391,731 A | 7/1983 | Boller et al. | 252/299.62 |
| 4,539,154 A | 9/1985 | Krebs | 260/410.9 |
| 4,739,098 A | 4/1988 | Chandraratna | 560/8 |
| 4,804,670 A | 2/1989 | Wuest et al. | 514/381 |
| 4,923,884 A | 5/1990 | Chandraratna | 514/354 |
| 4,927,947 A | 5/1990 | Chandraratna | 549/484 |
| 5,426,118 A | 6/1995 | Chandraratna et al. | 514/337 |
| 5,451,605 A | 9/1995 | Chandraratna et al. | 514/475 |
| 5,455,265 A | 10/1995 | Chandraratna | 514/448 |
| 5,470,999 A | 11/1995 | Chandraratna | 560/100 |
| 5,618,836 A | 4/1997 | Chandraratna et al. | 514/444 |
| 5,760,276 A | 6/1998 | Beard et al. | 560/102 |
| 5,877,207 A | 3/1999 | Klein et al. | 514/456 |

FOREIGN PATENT DOCUMENTS

| | | |
|---|---|---|
| EP | 0272921 | 6/1988 |
| WO | 93/11755 | 6/1993 |
| WO | 96/20930 | 7/1996 |

OTHER PUBLICATIONS

Dawson and William H. Okamura, *Chemistry and Biology of Synthetic Retinoids* published by CRC Press, Inc., 1990, pp. 334–335.
Negishi et al., "Conversion of Methyl Ketones into Terminal Acetylenes and (E)–Trisubstituted Olefins of Terpenoid Origin", *J. Org. Chem.* 45 No. 12, 1980 p. 2526.

Verma & Boutwell, Cancer Research, (1977), 37 2196–2201.
Cancer Research: 1662–1670 (1975).
Feigner P. L. and Holm M. (1989) Focus, 112.
Heyman et al., Cell 68, 397–406, (1992).
Allegretto et al., J. Biol. Chem. 268, 26625–26633.
Mangelsdorf et al., The Retinoids: Biology, Chemistry and Medicine, pp. 319–349, Raven Press Ltd., New York.
Cheng et al., Biochemical Pharmacology vol. 22 pp. 3099–3108.
Klein et al., J. Biol. Chem. 271, 22692–22696 (1996).
Chen et al. (1987) Mol. Cell. Biol. 7, 2745–2752.
de Wet (1987) Mol. Cell. Biol. 7, 725–737.
Nagpal et al., EMBO J. 12, 2349–2360 (1993).
Corey, E. J., Schmidt, G., *Tet. Lett.*, 399, (1979).
Omura, K., Swern D., *Tetrahedron*, 1978, 34, 1651.

*Primary Examiner*—James O. Wilson
*Assistant Examiner*—Leigh C. Maier
(74) *Attorney, Agent, or Firm*—Gabor L. Szekeres; Robert J. Baran; Martin A. Voet

(57) ABSTRACT

Compounds of the Formula 1, Formula 2, Formula 3 and Formula 4 wherein the symbols have the meaning assigned to them in the disclosure have retinoid-like biological activity.

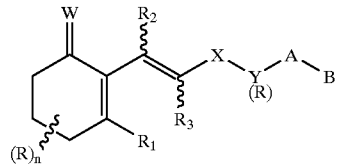

Formula 1

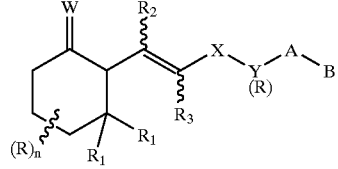

Formula 2

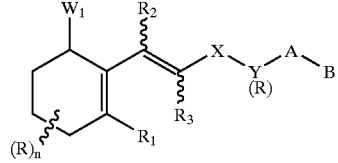

Formula 3

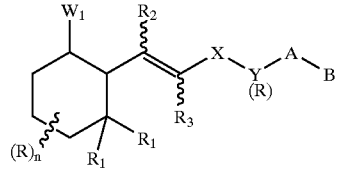

Formula 4

9 Claims, No Drawings

US 6,465,647 B1

OXYGEN, SULFUR AND NITROGEN SUBSTITUTED CYCLOHEXENE AND CYCLOHEXANE DERIVATIVES HAVING RETINOID-LIKE BIOLOGICAL ACTIVITY

CROSS-REFERENCE TO RELATED APPLICATION

The present application is a divisional of application Ser. No. 09/307,061 filed on May 7, 1999, to be issued as U.S. Pat. No. 6,166,244.

BACKGROUND OF THE INVENTION

1. Field of the Invention

The present invention relates to novel compounds having retinoid-like biological activity. More specifically, the present invention relates to aryl and heteroarylcyclohexenyl substituted or aryl and heteroarylcyclohexanyl substituted alkene derivatives which have retinoid-like, retinoid antagonist or retinoid inverse agonist-like biological activity.

2. Background Art

Compounds which have retinoid-like activity are well known in the art, and are described in numerous United States and other patents and in scientific publications. It is generally known and accepted in the art that retinoid-like activity is useful for treating animals of the mammalian species, including humans, for curing or alleviating the symptoms and conditions of numerous diseases and conditions. In other words, it is generally accepted in the art that pharmaceutical compositions having a retinoid-like compound or compounds as the active ingredient are useful as regulators of cell proliferation and differentiation, and particularly as agents for treating skin-related diseases, including, actinic keratoses, arsenic keratoses, inflammatory and non-inflammatory acne, psoriasis, ichthyoses and other keratinization and hyperproliferative disorders of the skin, eczema, a topic dermatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. Retinoid compounds are also useful for the prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, retinoid compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to increase the level of circulating tissue plasminogen activator (TPA). Other uses for retinoid compounds include the prevention and treatment of conditions and diseases associated with human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

Although pharmaceutical compositions containing retinoids have well established utility, retinoids also cause a number of undesired side effects at therapeutic dose levels, including headache, teratogenesis, mucocutaneous toxicity, musculoskeletal toxicity, dyslipidemias, skin irritation, headache and hepatotoxicity. These side effects limit the acceptability and utility of retinoids for treating disease.

It is now general knowledge in the art that two main types of retinoid receptors exist in mammals (and other organisms). The two main types or families of receptors are respectively designated the RARs and RXRs. Within each type there are subtypes; in the RAR family the subtypes are designated RAR$_\alpha$, RAR$_\beta$ and RAR$_\gamma$, in RXR the subtypes are: RXR$_\alpha$, RXR$_\beta$ and RXR$_\gamma$. It has also been established in the art that the distribution of the two main retinoid receptor types, and of the several sub-types is not uniform in the various tissues and organs of mammalian organisms. Moreover, it is generally accepted in the art that many unwanted side effects of retinoids are mediated by one or more of the RAR receptor subtypes. Accordingly, among compounds having agonist-like activity at retinoid receptors, specificity or selectivity for one of the main types or families, and even specificity or selectivity for one or more subtypes within a family of receptors, is considered a desirable pharmacological property. Some compounds bind to one or more RAR receptor subtypes, but do not trigger the response which is triggered by agonists of the same receptors. A compound that binds to a biological receptor but does not trigger an agonist-like response is usually termed an antagonist. Accordingly, the "effect" of compounds on retinoid receptors may fall in the range of having no effect at all, (inactive compound, neither agonist nor antagonist) or the compound may elicit an agonist-like response on all receptor subtypes (pan-agonist). As still another alternative a compound may be a partial agonist and/or partial antagonist of certain receptor subtypes if the compound binds to but does not activate certain receptor subtype or subtypes but elicits an agonist-like response in other receptor subtype or subtypes. A pan-antagonist is a compound that binds to all known retinoid receptors but does not elicit an agonist-like response in any of the receptors.

Recently a two-state model for certain receptors, including the above-mentioned retinoid receptors, have emerged. In this model, an equilibrium is postulated to exist between inactive receptors and spontaneously active receptors which are capable of coupling with a G protein in the absence of a ligand (agonist). In this model, so-called "inverse agonists" shift the equilibrium toward inactive receptors, thus bringing about an overall inhibitory effect. Neutral antagonists do not effect the receptor equilibrium but are capable of competing for the receptors with both agonists (ligands) and with inverse agonists. U.S. Pat. No. 5,877,207 titled "Synthesis and Use of Retinoid Compounds Having Negative Hormone and/or Antagonist Activities" describes the foregoing two-state model and the use of retinoid antagonist and negative hormones in detail.

In as much as naturally occurring retinoic acid includes a cyclohexene moiety, numerous patents and scientific publications which relate to the chemistry and biology of retinoids and related compounds are of interest as background to the present invention. Among the scientific publications Dawson and William H. Okamura, *Chemistry and Biology of Synthetic Retinoids*, published by CRC Press Inc., 1990, pages 334–335, 354 and 324–356 is of special interest as an overview of the prior art on the subject. The publication Negishi, Ei-ichi, Anthony O. King, and William L. Klima, "Conversion of Methyl Ketones into Terminal Acetylenes and (E)-Trisubstituted Olefins of Terpenoid Origin", *J. Org. Chem.* 45 No. 12, 1980 p. 2526 is of interest as it relates to a process of synthesizing certain cyclohexene derivatives.

Among the numerous United States and foreign patents which disclose compounds having retinoid agonist, antagonist or inverse agonist like biological activity and are known to applicant the following include a cyclohexane or cyclohexene ring structure and therefore are of interest as background to the present invention: U.S. Pat. No. 5,760,276; 5,618,836; 5,470,999; 5,451,605; 5,426,118; 4,539,154; 4,739,098; 4,923,884; 4,927,947 and EPO 0 272 921. U.S. Pat. No. 4,391,731; discloses certain cyclohexane derivatives suitable for use as liquid crystals.

SUMMARY OF THE INVENTION

The present invention relates to compounds of Formula 1, Formula 2, Formula 3 and Formula 4

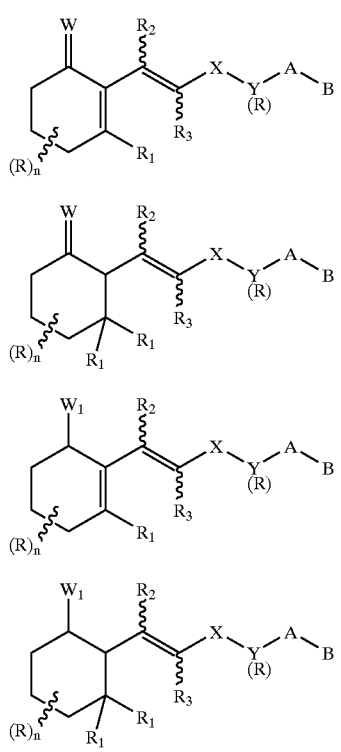

Formula 1

Formula 2

Formula 3

Formula 4 wherein R, $R_1$, $R_2$ and $R_3$ are H, lower alkyl of 1 to 10 carbons, cycloalkyl of 3 to 10 carbons, halogen, $(C_{1-10}$-lower alkyl$)_3$-silyl, $C_{1-10}$-lower alkylphenyl, or phenyl-$C_{1-10}$-lower alkyl.

n is an integer having the values of 0 to 6;

W is O, S, $C(R)_2$, $CRCO_2R$, NR, NOR, $NN(R)_2$;

$W_1$ is OR, SR, $N(R)_2$, RC(O)O, RC(S)O, RC(O)S, NRC(O)R, NRC(S)R, NRC(O)N(R)$_2$, NRC(S)N(R)$_2$, OC(O)OR, and SC(O)OR;

X is C≡C, C(O)O, C(O)S, CONR, CSNR, and (CR=CR)$_{n'}$ where n' is an integer having the values 1 to 5;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl and heteroaryl groups being optionally substituted with one or two R groups, or when X is —(CR=CR)$_{n'}$— and n' is 3, 4 or 5 then Y represents a direct valence bond between said (CR=CR)$_{n'}$ group and B;

A is $(CH_2)_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, or tri-lower alkylsilyl, where R$_7$ is an alkyl, cycloalkyl or alkenyl group containing 1 to 5 carbons, R$_8$ is an alkyl group of 1 to 10 carbons or trimethylsilylalkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons, or a pharmaceutically acceptable salt of said compound, with the proviso that when X is C≡C, Y is phenyl then in the compounds of Formula 1 W is not oxygen (O).

In a second aspect, this invention relates to the use of the compounds of Formula 1, 2, 3 and 4 for the treatment of skin-related diseases, including, without limitation, actinic keratoses, arsenic keratoses, inflammatory and non-inflammatory acne, psoriasis, ichthyoses and other keratinization and hyperproliferative disorders of the skin, eczema, a topic derrnatitis, Darriers disease, lichen planus, prevention and reversal of glucocorticoid damage (steroid atrophy), as a topical anti-microbial, as skin anti-pigmentation agents and to treat and reverse the effects of age and photo damage to the skin. The compounds are also useful for the prevention and treatment of metabolic diseases such as type II diabetes and diabetes mellitus and for prevention and treatment of cancerous and precancerous conditions, including, premalignant and malignant hyperproliferative diseases such as cancers of the breast, skin, prostate, cervix, uterus, colon, bladder, esophagus, stomach, lung, larynx, oral cavity, blood and lymphatic system, metaplasias, dysplasias, neoplasias, leukoplakias and papillomas of the mucous membranes and in the treatment of Kaposi's sarcoma. In addition, the present compounds can be used as agents to treat diseases of the eye, including, without limitation, proliferative vitreoretinopathy (PVR), retinal detachment, dry eye and other corneopathies, as well as in the treatment and prevention of various cardiovascular diseases, including, without limitation, diseases associated with lipid metabolism such as dyslipidemias, prevention of post-angioplasty restenosis and as an agent to. increase the level of circulating tissue plasminogen activator (TPA). Other uses for the compounds of the present invention include the prevention and treatment of conditions and diseases associated with Human papilloma virus (HPV), including warts and genital warts, various inflammatory diseases such as pulmonary fibrosis, ileitis, colitis and Krohn's disease, neurodegenerative diseases such as Alzheimer's disease, Parkinson's disease and stroke, improper pituitary function, including insufficient production of growth hormone, modulation of apoptosis, including both the induction of apoptosis and inhibition of T-Cell activated apoptosis, restoration of hair growth, including combination therapies with the present compounds and other agents such as Minoxidil$^R$, diseases associated with the immune system, including use of the present compounds as immunosuppressants and immunostimulants, modulation of organ transplant rejection and facilitation of wound healing, including modulation of chelosis.

Alternatively, those compounds of the invention which act as antagonists or inverse agonists of one or more retinoid receptor subtypes are useful to prevent certain undesired side effects of retinoids which are administered for the treatment or prevention of certain diseases or conditions. For this purpose the retinoid antagonist and/or inverse agonist compounds of the invention may be coadministered with retinoids. The retinoid antagonist and inverse agonist compounds of the present invention are also useful in the treatment of acute or chronic toxicity resulting from overdose or poisoning by retinoid drugs or Vitamin A.

This invention also relates to a pharmaceutical formulation comprising a compound of Formula 1, 2, 3 or 4 in admixture with a pharmaceutically acceptable excipient, said formulation being adapted for administration to a mammal, including a human being, to treat or alleviate the conditions which were described above as treatable by retinoids, to be co-administered with retinoids to eliminate or reduce side effects of retinoids, or to treat retinoid or Vitamin A overdose or poisoning.

BIOLOGICAL ACTIVITY, MODES OF ADMINISTRATION

Assays of Retinoid-like or Retinoid Antagonist and Inverse Agonist-like Biological Activity A classic measure of retinoic acid activity involves measuring the effects of retinoic acid on ornithine decarboxylase. The original work on the correlation between retinoic acid and a decrease in cell proliferation was done by Verma & Boutwell, Cancer Research, 1977, 37, 2196–2201. That reference discloses that ornithine decarboxylase (ODC) activity increased precedent to polyamine biosynthesis. It has been established elsewhere that increases in polyamine synthesis can be correlated or associated with cellular proliferation. Thus, if ODC activity could be inhibited, cell hyperproliferation could be modulated. Although all cases for ODC activity increases are unknown, it is known that 12-0-tetradecanoylphorbol-13-acetate (TPA) induces ODC activity. Retinoic acid inhibits this induction of ODC activity by TPA. An assay essentially following the procedure set out in Cancer Research: 1662–1670,1975 may be used to demonstrate inhibition of TPA induction of ODC by compounds of this invention. "IC$_{60}$" is that concentration of the test compound which causes 60% inhibition in the ODC assay. By analogy, "IC$_{80}$", for example, is that concentration of the test compound which causes 80% inhibition in the ODC assay.

Other assays described below, measure the ability of the compounds of the present invention to bind to, and/or activate various retinoid receptor subtypes. When in these assays a compound binds to a given receptor subtype and activates the transcription of a reporter gene through that subtype, then the compound is considered an agonist of that receptor subtype. Conversely, a compound is considered an antagonist of a given receptor subtype if in the below described co-tranfection assays the compound does not cause significant transcriptional activation of the receptor regulated reporter gene, but nevertheless binds to the receptor with a K$_d$ value of less than approximately 1 micromolar. In the below described assays the ability of the compounds to bind to RAR$_\alpha$, RAR$_\beta$, RAR$_\gamma$, RXR$_\alpha$, RXR$_\beta$ and RXR$_\gamma$ receptors, and the ability or inability of the compounds to activate transcription of a reporter gene through these receptor subtypes can be tested. These assays are expected to demonstrate that the compounds of the present invention act as agonists of one or more of the above-described receptors. However, some of the compounds of the invention may behave as retinoid antagonists or partial antagonists and/or as inverse agonists. Because of the complex distribution of the different retinoid receptors in various organs of the mammalian body partial agonists and partial antagonists and compounds which have the characteristics of both may lend themselves to particularly useful therapeutic applications and may avoid serious side effects of conventional retinoid drugs.

As far as specific assays are concerned to demonstrate the activities of the compounds of the present invention, a chimeric receptor transactivation assay which tests for agonist-like activity in the PAR$_\alpha$, RAR$_\beta$, RAR$_\gamma$, RXR$_\alpha$ receptor subtypes, and which is based on work published by Feigner P. L. and Holm M. (1989) Focus, 112 is described in detail in U.S. Pat. No. 5,455,265. The specification of U.S. Pat. No. 5,455,265 is hereby expressly incorporated by reference.

A holoreceptor transactivation assay and a ligand binding assay which measure the antagonist/agonist like activity of the compounds of the invention, or their ability to bind to the several retinoid receptor subtypes, respectively, are described in published PCT Application No. WO WO 93/11755 (particularly on pages 30–33 and 37–41) published on Jun. 24, 1993, the specification of which is also incorporated herein by reference. A detailed experimental procedure for holoreceptor transactivations has been described by Heyman et al. Cell 68, 397–406, (1992); Allegretto et al. J. Biol. Chem. 268, 26625–26633, and Mangelsdorf et al. The Retinoids: Biology, Chemistry and Medicine, pp 319–349, Raven Press Ltd., New York, which are expressly incorporated herein by reference. The results obtained in this assay are expressed in EC$_{50}$ numbers, as they are also in the chimeric receptor transactivation assay. The results of ligand binding assay are expressed in K$_d$ numbers. (See Cheng et al. Biochemical Pharmacology Vol. 22 pp 3099–3108, expressly incorporated herein by reference.)

Still another transactivation assay, the "PGR assay" is described in the publication Klein et al. J. Biol. Chem. 271, 22692–22696 (1996) which is expressly incorporated herein by reference, and a detailed description is also provided below. The results of the PGR assay are also expressed in EC$_{50}$ numbers (nanomolar concentration).

RAR-P-GR Holoreceptor Transactivation Assay

CV-1 cells (4×10$^5$ cells/well) were transiently transfected with the luciferase reporter plasmid MTV-4(R5G)-Luc (0.7 ug/well) containing four copies of the R5G retinoid DNA response element along with the RXRα expression plasmid pRS-hRXRα (0.1 ug/well) and one of the RAR-P-GR expression plasmids (0.05 ug/well) in 12 well plates via calcium phosphate precipitation Chen et al. (1987) Mol. Cell. Biol. 7, 2745–2752 as described by Klein et al. in J. Biol. Chem. 271, 22692, referenced above. The three different RAR-P-GR expression plasmids, pRS-RARα-P-GR, pcDNA3-RARβ-P-GR and pcDNA3-RARγ-P-GR, express RAR$_\alpha$, RAR$_\beta$ and RARγ receptors, respectively, which contain modified DNA binding domains such that their "P-boxes" have been altered to that of the glucocorticoid receptor. These RAR-P-GR receptors bind to DNA as heterodimeric complexes with RXR. Specifically, the RAR-P-GR receptors bind retinoic acid response elements designated R5G, comprised of two RAR half sites (nucleotide sequence 5'-GGTTCA-3') separated by 5 base pairs in which the 3'-half site has been modified to that of a glucocorticoid receptor half site, 5'-AGAACA-3'. To allow for various in transfection efficiency a β-galactosidase expression plasmid (0.01 ug/well) was used as an internal control. Alternatively, the assay was performed in a 96-well microtiter plate format (5000 cells/well) in a manner which was identical to that described above except ⅕ of the amount of the DNA-calcium phosphate precipitant (20 μl instead of 100 μl) was applied to each well. Eighteen hours after introduction of the DNA precipitants, cells were rinsed with phosphate buffered saline (PBS) and fed with D-MEM (Gibco-BRL) containing 10% activated charcoal extracted fetal bovine serum (Gemini Bio-Products). Cells were treated for 18 hours with the compounds indicated in the figures. After rinsing with PBS cells were lysed with luciferase activity was measured as previously described in de Wet (1987) Mol. Cell. Biol. 7, 725–737. Luciferase values represent the mean±SEM of triplicate determinations normalized to β-galactosidase activity.

Inverse agonists are ligands that are capable of inhibiting the basal receptor activity of unliganded receptors. Recently, retinoic acid receptors (RARs) have been shown to be responsive to retinoid inverse agonists in regulating basal gene transcriptional activity. Moreover, the biological effects associated with retinoid inverse agonists are distinct from those of retinoid agonists or antagonists. For example, RAR inverse agonists, but not RAR neutral antagonists, cause a dose-dependent inhibition of the protein MRP-8 in cultured human keratinocytes differentiated with serum. MRP-8 is a specific marker of cell differentiation, which is also highly expressed in psoriatic epidermis, but is not detectable in normal human skin. Thus, retinoid inverse agonists may offer a unique way of treating diseases such as psoriasis.

The activity of retinoid inverse agonists can be tested by the procedure of Klein et al. *J. Biol. Chem.* 271, 22692–22696 (1996) which is expressly incorporated herein by reference. In this assay, retinoid inverse agonists are able to repress the basal activity of a RARγ-VP- 16 chimeric receptor where the constituitively active domain of the herpes simplex virus (HSV) VP-16 is fused to the N-terminus of RAR$_γ$. CV-1 cells are cotransfected with RARγ-VP-16, an ER-RXRα chimeric receptor and an ERE-tk-Luc chimeric reporter gene to produce a basal level of luciferase activity, as shown by Nagpal et al. *EMBO J.* 12, 2349–2360 (1993) expressly incorporated herein by reference. Retinoid inverse agonists are able to inhibit the basal luciferase activity in these cells in a dose dependent manner and IC$_{50}$s measured. A detailed description of the tests used for determining whether or not a compound is a retinoid antagonist or inverse agonist, and the manner of utilizing retinoid antagonists and inverse agonists is provided in U.S. Pat. No. 5,877,207, the specification of which is expressly incorporated herein by reference.

Table 1 discloses the activity of certain exemplary compounds of the invention in the above-described oinithine decarboxylase (ODC) assay.

TABLE 1

Ornithine Decarboxylase (ODC) Assay

| Compound # | IC$_{60}$ (nanomolar) |
|---|---|
| 3a | 0.52 |
| 3b | 4.3 |
| 4a | 20.9 |
| 5a | 15.7 |
| 5b | 234 |
| 6a | 5.1 |
| 6b | 124 |
| 7a | 8.6 |
| 10 | 2.4 |
| 11 | 10.3 |
| 12 | 7.8 |

Modes of Administration

The compounds of this invention may be administered systemically or topically, depending on such considerations as the condition to be treated, need for site-specific treatment, quantity of drug to be administered, and numerous other considerations. Thus, in the treatment of dermatoses, it will generally be preferred to administer the drug topically, though in certain cases such as treatment of severe cystic acne or psoriasis, oral administration may also be used. Any common topical formulation such as a solution, suspension, gel, ointment, or salve and the like may be used. Preparation of such topical formulations are well described in the art of pharmaceutical formulations as exemplified, for example, by Remington's Pharmaceutical Science, Edition 17, Mack Publishing Company, Easton, Pennsylvania. For topical application, these compounds could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases,. it may be useful to formulate these compounds by injection. In certain cases, it may be useful to formulate these compounds in suppository form or as extended release formulation for deposit under the skin or intramuscular injection.

Other medicaments can be added to such topical formulation for such secondary purposes as treating skin dryness; providing protection against light; other medications for treating dermatoses; medicaments for preventing infection, reducing irritation, inflammation and the like.

Treatment of dermatoses or any other indications known or discovered to be susceptible to treatment by retinoic acid-like compounds will be effected by administration of the therapeutically effective dose of one or more compounds of the instant invention. A therapeutic concentration will be that concentration which effects reduction of the particular condition, or retards its expansion. In certain instances, the compound potentially may be used in prophylactic manner to prevent onset of a particular condition.

A useful therapeutic or prophylactic concentration will vary from condition to condition and in certain instances may vary with the severity of the condition being treated and the patient's susceptibility to treatment. Accordingly, no single concentration will be uniformly usefuil, but will require modification depending on the particularities of the disease being treated. Such concentrations can be arrived at through routine experimentation. However, it is anticipated that in the treatment of, for example, acne, or similar dermatoses, that a formulation containing between 0.01 and 1.0 milligrams per milliliter of formulation will constitute a therapeutically effective concentration for total application. If administered systemically, an amount between 0.01 and 5 mg per kg of body weight per day would be expected to effect a therapeutic result in the treatment of many diseases for which these compounds are useful.

The partial or pan retinoid antagonist and/or retinoid inverse agonist compounds of the invention, when used to take advantage of their antagonist and/or inverse agonist property, can be co-administered to mammals, including humans, with retinoid agonists and, by means of pharmacological selectivity or site-specific delivery, preferentially prevent the undesired effects of certain retinoid agonists. The antagonist and/or inverse agonist compounds of the invention can also be used to treat Vitamin A overdose, acute or chronic, resulting either from the excessive intake of vitamin A supplements or from the ingestion of liver of certain fish and animals that contain high levels of Vitamin A. Still further, the antagonist and/or inverse agonist compounds of the invention can also be used to treat acute or chronic toxicity caused by retinoid drugs. It has been known in the art that the toxicities observed with hypervitaminosis A syndrome (headache, skin peeling, bone toxicity, dyslipidemias) are similar or identical with toxicities observed with other retinoids, suggesting a common biological cause, that is RAR activation. Because the antagonist or inverse agonist compounds of the present invention block or diminish RAR activation, they are suitable for treating the foregoing toxicities.

Generally speaking, for therapeutic applications in mammals, the antagonist and/or inverse agonist compounds of the invention can be admistered enterally or topically as an antidote to vitamin A, or antidote to retinoid toxicity resulting from overdose or prolonged exposure, after intake of the causative factor (vitamin A, vitamin A precursor, or other retinoid) has been discontinued. Alternatively, the antagonist and/or inverse agonist compounds of the invention are co-administered with retinoid drugs, in situations where the retinoid provides a therapeutic benefit, and where the co-administered antagonist and/or inverse agonist compound alleviates or eliminates one or more undesired side effects of the retinoid. For this type of application the antagonist and/or inverse agonist compound may be administered in a site-specific manner, for example as a topically applied cream or lotion while the co-administered retinoid may be given enterally. For therapeutic applications the antagonist compounds of the invention, like the retinoid agonists compounds, are incorporated into pharmaceutical compositions, such as tablets, pills, capsules, solutions, suspensions, creams, ointments, gels, salves, lotions and the like, using such pharmaceutically acceptable excipients and vehicles which per se are well known in the art. For topical application, the antagonist and/or inverse agonist compounds of the invention could also be administered as a powder or spray, particularly in aerosol form. If the drug is to be administered systemically, it may be confected as a powder, pill, tablet or the like or as a syrup or elixir suitable for oral administration. For intravenous or intraperitoneal administration, the compound will be prepared as a solution or suspension capable of being administered by injection. In certain cases, it may be useful to formulate these compounds by injection. In certain cases, it may be useful to formulate these compounds in suppository form or as extended release formulation for deposit under the skin or intramuscular injection.

The antagonist and/or inverse agonist compounds also, like the retinoid agonists of the invention, will be administered in a therapeutically effective dose. A therapeutic concentration will be that concentration which effects reduction of the particular condition, or retards its expansion. When co-administering the compounds of the invention to block retinoid-induced toxicity or side effects, the antagonist and/or inverse agonist compounds of the invention are used in a prophylactic manner to prevent onset of a particular condition, such as skin irritation.

A useful therapeutic or prophylactic concentration will vary from condition to condition and in certain instances may vary with the severity of the condition being treated and the patient's susceptibility to treatment. Accordingly, no single concentration will be uniformly useful, but will require modification depending on the particularities of the chronic or acute retinoid toxicity or related condition being treated. Such concentrations can be arrived at through routine experimentation. However, it is anticipated that a formulation containing between 0.01 and 1.0 milligrams of the active compound per mililiter of formulation will constitute a therapeutically effective concentration for total application. If administered systemically, an amount between 0.01 and 5 mg per kg per day of body weight would be expected to effect a therapeutic result.

GENERAL EMBODIMENTS AND SYNTHETIC METHODOLOGY

Definitions

The term alkyl refers to and covers any and all groups which are known as normal alkyl, branched-chain alkyl and cycloalkyl. The term alkenyl refers to and covers normal alkenyl, branch chain alkenyl and cycloalkenyl groups having one or more sites of unsaturation. Similarly, the term alkynyl refers to and covers normal alkynyl, and branch chain alkynyl groups having one or more triple bonds.

Unless specified otherwise, lower alkyl means the above-defined broad definition of alkyl groups having 1 to 6 carbons in case of normal lower alkyl, and as applicable 3 to 6 carbons for lower branch chained and cycloalkyl groups. Lower alkenyl is defined similarly having 2 to 6 carbons for normal lower alkenyl groups, and 3 to 6 carbons for branch chained and cyclo- lower alkenyl groups. Lower alkynyl is also defined similarly, having 2 to 6 carbons for normal lower alkynyl groups, and 4 to 6 carbons for branch chained lower alkynyl groups.

The term "ester" as used here refers to and covers any compound falling within the definition of that term as classically used in organic chemistry. It includes organic and inorganic esters. Where B of Formula 1, 2, 3 or 4 is —COOH, this term covers the products derived from treatment of this function with alcohols or thiols preferably with aliphatic alcohols having 1–6 carbons. Where the ester is derived-from compounds where B is —CH$_2$OH, this term covers compounds derived from organic acids capable of forming esters including phosphorous based and sulfur based acids, or compounds of the formula —CH$_2$OCOR$_{11}$ where R$_{11}$ is any substituted or unsubstituted aliphatic, aromatic, heteroaromatic or aliphatic aromatic group, preferably with 1–6 carbons in the aliphatic portions.

Unless stated otherwise in this application, preferred esters are derived from the saturated aliphatic alcohols or acids of ten or fewer carbon atoms or the cyclic or saturated aliphatic cyclic alcohols and acids of 5 to 10 carbon atoms. Particularly preferred aliphatic esters are those derived from lower alkyl acids and alcohols. Also preferred are the phenyl or lower alkyl phenyl esters.

Amides has the meaning classically accorded that term in organic chemistry. In this instance it includes the unsubstituted amides and all aliphatic and aromatic mono- and di-substituted amides. Unless stated otherwise in this application, preferred amides are the mono- and di-substituted amides derived from the saturated aliphatic radicals of ten or fewer carbon atoms or the cyclic or saturated aliphatic-cyclic radicals of 5 to 10 carbon atoms. Particularly preferred amides are those derived from substituted and unsubstituted lower alkyl amines. Also preferred are mono- and disubstituted amides derived from the substituted and unsubstituted phenyl or lower alkylphenyl amines. Unsubstituted amides are also preferred.

Acetals and ketals include the radicals of the formula -CK where K is (—OR)$_2$. Here, R is lower alkyl. Also, K may be —OR$_7$O— where R$_7$ is lower alkyl of 2-5 carbon atoms, straight chain or branched.

A pharmaceutically acceptable salt may be prepared for any compound in this invention having a functionality capable of forming a salt, for example an acid functionality. A pharmaceutically acceptable salt is any salt which retains the activity of the parent compound and does not impart any deleterious or untoward effect on the subject to which it is administered and in the context in which it is administered.

Pharmaceutically acceptable salts may be derived from organic or inorganic bases. The salt may be a mono or polyvalent ion. Of particular interest are the inorganic ions, sodium, potassium, calcium, and magnesium. Organic salts may be made with amines, particularly ammonium salts such as mono-, di- and trialkyl amines or ethanol amines. Salts may also be formed with caffeine, tromethamine and similar molecules. Where there is a nitrogen sufficiently basic as to be capable of forming acid addition salts, such may be formed with any inorganic or organic acids or alkylating agent such as methyl iodide. Preferred salts are those formed with inorganic acids such as hydrochloric acid, sulfuric acid or phosphoric acid. Any of a number of simple organic acids such as mono-, di- or tri- acid may also be used.

Many compounds of the present invention have trans and cis (E and Z) isomers. Specific orientation of substituents relative to a double bond is indicated in the name of the respective compound, and/or by specifically showing in the structural formula the orientation of the substituents relative to the double bond. Unless it is specifically stated otherwise the invention covers trans as well as cis isomers.

Some of the compounds of the present invention may contain one or more chiral centers and therefore may exist in enantiomeric and diastereomeric forms. The scope of the present invention is intended to cover all isomers per se, as well as mixtures of cis and trans isomers, mixtures of diastereomers and racemic mixtures of enantiomers (optical isomers) as well.

The compounds of the invention, can generally speaking be obtained by a series of reactions starting with a cyclohexen-1-one or cyclohexan-1-one derivative of Formula 5 where the dotted bond indicates the presence or absence of a bond, Z is iodine (I) or trimethylsilyl and the remaining symbols have the meaning assigned to them in connection with Formulas 1, 2, 3 and 4.

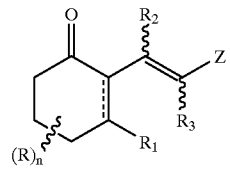

Formula 5

The cyclohexen-1-one or cyclohexan-1-one derivatives of Formula 5 can, generally speaking, be obtained as described in U.S. Pat. No. 5,760,276 the specification of which is incorporated herein by reference. An example of a starting compound within the scope of Formula 5, and one which is utilized for the synthesis of several preferred compounds of the invention is 2-(2-iodoethenyl)-3-methyl-2-cyclohexen-1-one (designated Compound 4, in U.S. Pat. No. 5,760,276). Another example of a starting compound that is utilized for the synthesis of several preferred compounds of the invention is 2-(2-[(trimethyl)silylethenyl]-3,3-dimethyl-2-cyclohexan-1-one that can be obtained by reacting 2-[2-(trimethyl)silylethenyl]-3-methyl-2-cyclohexen-1-one with methyllithium and copper (1) iodide under conditions described in the '276 patent. In accordance with a generalized methodology for obtaining compounds of the invention the starting compounds of Formula 5, or readily available derivatives thereof, are reacted with an ethynylaryl or ethynylheteroaryl derivative of the formula HC≡C—Y(R)—A—B in the presence of a suitable catalyst to obtain compounds of the invention where the X group is C≡C. The symbols Y, R, A and B are defined as in connection with Formulas 1, 2, 3 and 4.

To obtain compounds of the invention where the X group is —(CR=CR)$_n$—, generally speaking, a compound of Formula 5 where Z is iodine (I) is reacted with tributylstannylethoxyethene followed by one or more Horner Emmons or Wittig reaction to provide a polyene chain. Compounds of the invention where the X group is COO, COS, or CONH can, generally speaking, be obtained by reacting a compound of Formula 5 where Z is iodine (I) with carbon monoxide and an aryl or heteroaryl reagent having a fonnula selected from HO—Y(R)—A—B, HS—Y(R)—A—B, and H$_2$N—Y(R)—A—B (the symbols Y, R, A and B are defined as in connection with Formulas 1, 2, 3 and 4) in the presence of a palladium catalyst, such as palladium (II) acetate.

Compounds of the invention where the W or W$_1$ group of Formulas 1, 2, 3 and 4, as applicable, is other than the oxo group shown in Formula 5 can, generally speaking, be obtained by reacting the cyclohexene- 1-one or cyclohexane-1-one compounds of the invention with a suitable reagent to modify the oxo group. For example the oxime derivatives, where with reference to Formulas 1, 2, 3 and 4 W is NOR, can be obtained by reacting the corresponding oxo compound with hydroxylamine. The Schiff base type derivatives, (W is NR) and hydrazone derivatives can be obtained, respectively, by reacting the oxo compounds with an amine of the formula RNH$_2$ or with a hydrazine derivative of the formula H$_2$NN(R)$_2$. Compounds of the invention where the C-1 carbon of the cycloalkyl ring is sp$^3$ hybridized, such as compounds of Formulas 3 and 4 can, generally speaking, be obtained by reactions which involve reduction of the C-1 ketone function of the cyclohexen-1-one or cyclohexane-1-one derivatives of the invention. Alternatively, these reactions can be performed on intermediates leading to compounds of the invention.

The synthetic methodology employed for the synthesis of the compounds of the present invention may also include transformations of the group designated B in Formulas 1, 2, 3 and 4. Generally speaking, these transformations involve reactions well within the skill of the practicing organic chemist. In this regard the following well known and published general principles and synthetic methodology are briefly described.

Carboxylic acids are typically esterified by refluxing the acid in a solution of the appropriate alcohol in the presence of an acid catalyst such as hydrogen chloride or thionyl chloride. Alternatively, the carboxylic acid can be condensed with the appropriate alcohol in the presence of dicyclohexylcarbodiimide (DCC) and 4-(dimethylamino)pyridine (DMAP). The ester is recovered and purified by conventional means. Acetals and ketals are readily made by the method described in March, "Advanced Organic Chemistry," 2nd Edition, McGraw-Hill Book Company, p 810). Alcohols, aldehydes and ketones all may be protected by forming respectively, ethers and esters, acetals or ketals by known methods such as those described in McOmie, Plenum Publishing Press, 1973 and *Protecting Groups*, Ed. Greene, John Wiley & Sons, 1981.

The acids and salts derived from compounds of the invention are readily obtainable from the corresponding esters. Basic saponification with an alkali metal base will provide the acid. For example, an ester of the invention may be dissolved in a polar solvent such as an alkanol, preferably under an inert atmosphere at room temperature, with about a three molar excess of base, for example, lithium hydroxide or potassium hydroxide. The solution is stirred for an extended period of time, between 15 and 20 hours, cooled, acidified and the hydrolysate recovered by conventional means.

The amide may be formed by any appropriate amidation means known in the art from the corresponding esters or carboxylic acids. One way to prepare such compounds is to convert an acid to an acid chloride and then treat that compound with ammonium hydroxide or an appropriate amine. For example, the ester is treated with an alcoholic base solution such as ethanolic KOH (in approximately a 10% molar excess) at room temperature for about 30 minutes. The solvent is removed and the residue taken up in an organic solvent such as diethyl ether, treated with a dialkyl formamide and then a 10-fold excess of oxalyl chloride. This is all effected at a moderately reduced temperature between about −10 degrees and +10 degrees C. The last mentioned solution is then stirred at the reduced temperature for 1–4 hours, preferably 2 hours. Solvent removal provides a residue which is taken up in an inert organic solvent such as benzene, cooled to about 0 degrees C. and treated with concentrated ammonium hydroxide. The resulting mixture is stirred at a reduced temperature for 1–4 hours. The product is recovered by conventional means.

Alcohols are made by converting the corresponding acids to the acid chloride with thionyl chloride or other means (J. March, "Advanced Organic Chemistry", 2nd Edition, McGraw-Hill Book Company), then reducing the acid chloride with sodium borohydride (March, Ibid, pg. 1124), which gives the corresponding alcohols. Alternatively, esters may be reduced with lithium aluminum hydride at reduced temperatures. Alkylating these alcohols with appropriate alkyl halides under Williamson reaction conditions (March, Ibid, pg. 357) gives the corresponding ethers. These alcohols can be converted to esters by reacting them with appropriate acids in the presence of acid catalysts or dicyclohexylcarbodiimide and dimethylaminopyridine.

Aldehydes can be prepared from the corresponding primary alcohols using mild oxidizing agents such as pyridinium dichromate in methylene chloride (Corey, E. J., Schmidt, G., *Tet. Lett.*, 399, 1979), or dimethyl sulfoxide/oxalyl chloride in methylene chloride (Omura, K., Swern, D., *Tetrahedron*, 1978, 34, 1651).

Ketones can be prepared from an appropriate aldehyde by treating the aldehyde with an alkyl Grignard reagent or similar reagent followed by oxidation.

Acetals or ketals can be prepared from the corresponding aldehyde or ketone by the method described in March, Ibid, p 810.

SPECIFIC EMBODIMENTS

With reference to the symbol Y in Formulas 1, 2, 3 and 4 the preferred compounds of the invention are those where Y is phenyl, naphthyl, pyridyl, thienyl or furyl. Even more preferred are compounds where Y is phenyl. As far as substititutions on the Y (phenyl) and Y (pyridyl) groups are concerned, compounds are preferred where the phenyl group is 1,4 (para) substituted and where the pyridine ring is 2,5 substituted. (Substitution in the 2,5 positions in the "pyridine" nomenclature corresponds to substitution in the 6-position in the "nicotinic acid" nomenclature.) In the presently preferred compounds of the invention there is no R substituent on the Y group.

The A—B group of the preferred compounds is $(CH_2)_qCOOH$ or $(CH_2)_q$—$COOR_8$, where $R_8$ is defined as above. Even more preferably q is zero and $R_8$ is lower alkyl or (trialkyl)silylethyl (or alkyl) more preferably (trimethyl) silylethyl.

In the presently preferred compounds of the invention X is an ethynyl (—C≡C—) group. However, compounds are also preferred in accordance with the invention where X is —(CR=CR)$_n$—, —CO—NR—, COO and COS—.

The W group of the compounds of Formulas 1 and 2 is preferably O (ketone) and NOR (oxime and alkoxime) where R is preferably H, lower alkyl, even more preferably methyl, or benzyl. Compounds of Formulas 1 and 2 where W is $CRCO_2R$ are also preferred, with W as CHCOOEt being even more preferred.

The $W_1$ group of the compounds of Formulas 3 and 4 is preferably OR where R is preferably hydrogen, or OC(O)R where R is preferably straight or branch-chained lower alkyl or phenyl. The carbon in the cyclohexene or cyclohexane ring of Formulas 3 and 4 is a chiral center, and compounds are also preferred where the respective dextrorotary and levorotatory enantiomers of these alcohols and or esters are separated in pure or substantially pure state.

The $R_1$, $R_2$, and $R_3$ groups of the compounds of the invention preferably are H, lower alkyl of 1 to 6 carbons, and more preferably H or methyl. Methyl is especially preferred for $R_1$ whereas H is especially preferred for $R_2$ and $R_3$.

The presently most preferred compounds of the invention are disclosed in Table 2 below with reference to Formulas 6, 7 and 8.

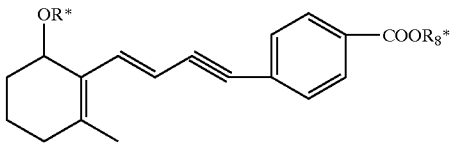

Formula 6

Formula 7

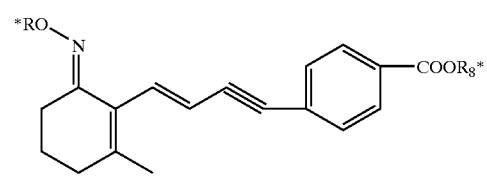

Formula 8

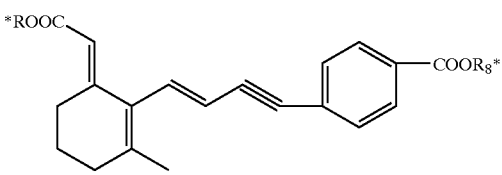

TABLE 2

| Compound # | Formula # | R* | $R_8$* | (−) or (+) enantiomer or racemate |
|---|---|---|---|---|
| 1 | 6 | H | Et | racemate |
| 1a | 6 | H | Et | (−) |
| 1b | 6 | H | Et | (+) |
| 2 | 6 | H | trimethyl-silylethyl | racemate |
| 3a | 6 | $CH_3CO$— | Et | (−) |
| 3b | 6 | $CH_3CO$ | Et | (+) |
| 4a | 6 | $CH_3CH_2CO$ | Et | (−) |
| 4b | 6 | $CH_3CH_2CO$ | Et | (+) |
| 5a | 6 | $(CH_3)_2CHCO$ | Et | (−) |
| 5b | 6 | $(CH_3)_2CHCO$ | Et | (+) |
| 6a | 6 | $(CH_3)_3CCO$ | Et | (−) |
| 6b | 6 | $(CH_3)_3CCO$ | Et | (+) |
| 7a | 6 | $C_6H_5CO$ | Et | (−) |
| 7b | 6 | $C_6H_5CO$ | Et | (+) |
| 2a | 6 | H | trimethyl-silylethyl | (−) |
| 8a | 6 | $CH_3CO$ | trimethyl-silylethyl | (−) |
| 8b | 6 | $CH_3CO$ | trimethyl-silylethyl | (+) |
| 9a | 6 | $CH_3CO$ | H | (−) |
| 9b | 6 | $CH_3CO$ | H | (+) |
| 10 | 7 | $CH_3$ | Et | — |
| 11 | 7 | $C_6H_5CH_2$— | Et | — |
| 12 | 8 | Et | Et | — |

The compounds of this invention can be made by the general procedures outlined above under the title "GENERAL EMBODIMENTS AND SYNTHETIC METHODOLOGY". The following chemical pathways represent the presently preferred synthetic routes to certain classes of the compounds of the invention and to certain specific exemplary compounds. However, the synthetic chemist will readily appreciate that the conditions set out here for these specific embodiments can be generalized to any and all of the compounds represented by Formulas 1, 2, 3 and 4.

Referring now to Reaction Scheme 1 a synthetic process is described whereby compounds of the invention are obtained in which, with reference to Formulas 1 and 3 the X group is an ethynyl (—C≡C—) function.

REACTION SCHEME 1

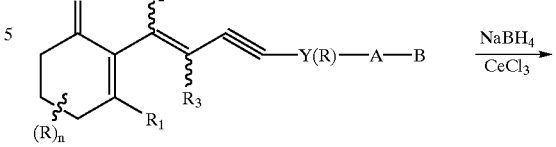

Formula 9
U.S. Pat. No. 5,760,276

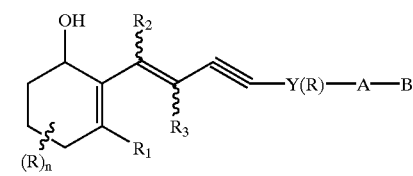

Formula 10

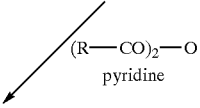

pyridine

Formula 11

The starting compound of Formula 9 shown in Reaction Scheme 1 is a 1-aryl or 1-heteroaryl 4-(cyclohex-2-en-1-one-2-yl)-but-1-yn-3-ene derivative which can be obtained in accordance with the teachings of U.S. Pat. No. 5,760,276. Ethyl 4-(4-(3-methyl-2-cyclohexen-1-on-2-yl)but-3-en-1-yn-1-yl)benzoate, described in Column 27 of the '276 patent as Compound 5 serves as an example, and is the starting compound for the synthesis of several preferred compounds of the present invention. Other examples are ethyl 5-(4-(3-methyl-2-cyclohexen-1-on-2-yl)but-3-en-1-yn-1-yl)pyridine-2-carboxylate, and ethyl 5-(4-(3-methyl-2-cyclohexen-1-on-2-yl)but-3-en-1-yn-1-yl)thiophene-2-carboxylate and ethyl 5-(4-(3-methyl-2-cyclohexen-1-on-2-yl)but-3-en-1-yn-1-yl)furan-2-carboxylate.

The ketone finction of the compounds of Formula 9 is reduced by reaction with sodium borohydride and cerium trichloride to provide 1-aryl or 1-heteroaryl 4-(6-hydroxy-cyclohex-1-enyl)-but-1-yn-3-ene derivatives of Formula 10. An assymetric center is formed on C-6 of the cyclohexene ring and the reaction usually provides the product as a mixture of compounds with R and S configuration at the newly formed asymetric carbon. Thus in the absence of a pre-existing chiral center in the compound a racemic mixture is formed by the reduction. Reaction Scheme 1 illustrates, as an example, the reaction of acylating the 6-hydroxyl group of the compounds of Formula 10 with an acid anhydride to provide the 1-heteroaryl 4-(6-acyloxy-cyclohex-1-enyl)-but-1-yn-3-ene derivatives of Formula 11.

Instead of acylation, the 6-hydroxyl group of the compounds of Formula 10 can be subjected to other reactions which are per se well known in the art (such as alkylation) to provide further compounds of the invention. Moreover, transformations of the A—B groups in accordance with reactions well known in the art, such as homologation, saponification, esterification and the like, as described above, provide further homologs and derivatives of the compounds of Formula 11.

REACTION SCHEME 2

Formula 10
racemic vinyl acetate toluene
enzyme
→

Formula 12
(+) enantiomer only

+

Formula 10
(−) enantiomer

REACTION SCHEME 3

Formula 13
U.S. Pat. No. 5,760,276     TMS = (trimethylsilyl)

NaBH₄
CeCl₃
→

Formula 14
racemic enzyme
vinyl acetate

Formula 15
(+) enantiomer

+

Formula 14
(−)enantiomer

Formula 15
(+) enantiomer triethylammonium flouride
hydrate
→

Formula 16
(+) enantiomer

Formula 14
(−) enantiomer triethylammonium flouride
hydrate
→

Formula 17
(−)enantiomer

Referring now to Reaction Schemes 2 and 3, the preparation of enantiomerically (optically) pure exemplary preferred compounds of the invention is disclosed. As is shown in Scheme 2, the hydroxyl function of the 1-aryl or 1-heteroaryl 4-(6-hydroxy-cyclohex-1-enyl)-but-1-yn-3-ene derivatives of Formula 10 is acetylated in a transesterification reaction with vinyl acetate in the presence of an enzyme that selectively catalyzes only the formation of a dextrorotatory (+) acetate ester. The enzyme used in this reaction is known as *pseudomonas cepacia* lipase, and is available from Altus Inc. Cambride Massachussets under the product name ChiroCLEC-PC. The product of the transesterification reaction is a dextrorotatory (+) 1-heteroaryl 4-(6-acetyloxy-cyclohex-1-enyl)-but-1-yn-3-ene derivative of Formula 12. The unreacted opposite (levorotatory) enantiomer 6-hydroxyl compound can also be isolated from the reaction mixture.

Reaction Scheme 3 illustrates preparation of exemplary compounds of the invention where the B group of Formula 1 is a free carboxylic acid (or a salt thereof), the C-6 carbon of the cyclohexene moiety is sp hybridized and the resulting chiral compounds are enantiomerically pure. The starting compounds in this sequence of reactions are 1-aryl or 1-heteroaryl 4-(cyclohex-2-en-one-2-yl)-but-1-yn-3-ene derivatives of Formula 13 where the B group of Formula 1 is a carboxylic acid esterified with a (timethylsilyl)ethyl group. Compounds of Formula 13 can be obtained in accordance with the teachings of U.S. Pat. No. 5,760,276. The ketone function of the compounds of Formula 13 is reduced with sodium borohydride and cerium trichloride to provide the corresponding racemic 6-hydroxy-cyclohex-2-ene derivatives of Formula 14. The 6-hydroxy-cyclohex-2-ene derivatives of Formula 14 are acetylated in transesterification reactions with vinyl acetate in the presence of the *pseudomonas cepacia* lipase enzyme, as described above in connection with Reaction Scheme 2, to result in the selective the formation of dextrorotatory (+) 6-acetyloxy-cyclohex-2-ene derivatives of Formula 15. The unreacted levorotatory 6-hydroxy-cyclohex-2-ene derivatives of Formula 14 can also be isolated from the reaction mixture, as indicated in the scheme.

Enantiomerically pure (or substantially pure) dextrorotatory (+) 6-acetyloxy-cyclohex-2-ene derivatives of Formula 16 having a free carboxylic acid function (or salt thereof), and enantiomerically pure (or substantially pure) levorotatory (−) 6-hydroxy-cyclohex-2-ene derivatives of Formula 17 having a free carboxylic acid function (or salt thereof), respectively, can be obtained by removal of the (trimethyl) silylethyl group by treatment of the corresponding (trimethyl)silylethyl esters (Formula 15 and 14) with triethylammonium fluoride.

REACTION SCHEME 4

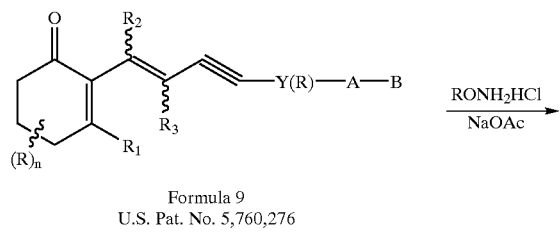

Formula 9
U.S. Pat. No. 5,760,276

$\xrightarrow{\text{RONH}_2\text{HCl}}{\text{NaOAc}}$

-continued

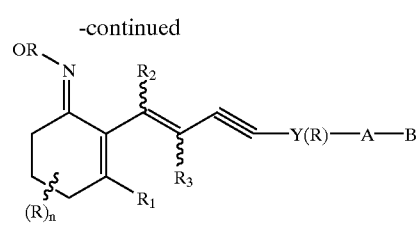

Formula 18

HOMOLOGS AND DERIVATIVES

Reaction Scheme 4 discloses the preparation of exemplary compounds of the invention where the group designated W in Formula 1 is NOR. R is defined as in connection with Formula 1. Thus, this scheme illustrates the formation of oxime, alkoxime, phenyloxime, benzyloxime and related derivatives. In accordance with this scheme, a 1-aryl or 1-heteroaryl 4-(cyclohex-2-en-one-2-yl)-but-1-yn-3-ene derivative of Formula 9 is reacted with a reagent of the formula RONH$_2$ HCl in the presence of sodium acetate to provide the oxime, alkoxime, phenyloxime or benzyloxime derivative of Formula 18. Examples of reagents suitable for this reaction are hydroxylamine hydrochloride, methoxylamine hydrochloride and benzyloxyamine hydrochloride. Compounds of the invention where the group designated W in Formula 1 is NR and NN(R)$_2$ (Schiff base derivatives and hydrazones) can be made by analogous reactions, that is by reacting the 1-aryl or 1-heteroaryl 4-(cyclohex-2-en-1-one-2-yl)-but-1-yn-3-ene derivatives of Formula 9 with an amine of the formula H$_2$NR or with a hydrazine of the formula H$_2$NN(R)$_2$, respectively. These reactions are also typically performed with the hydrochloride salts of the amine or hydrazine reagents in the presence of sodium acetate.

REACTION SCHEME 5

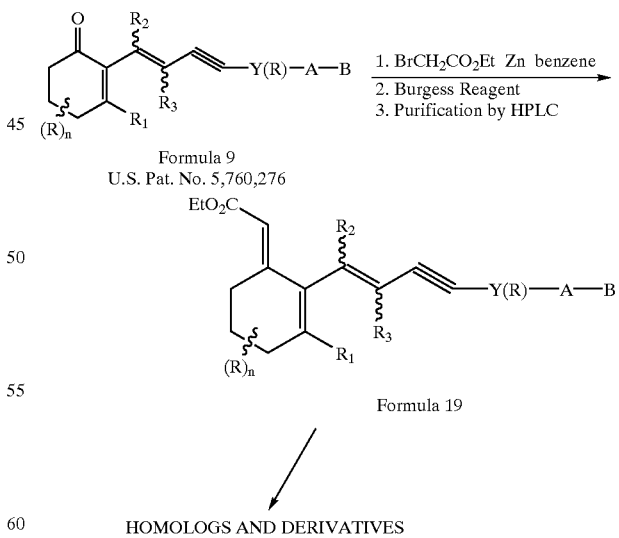

HOMOLOGS AND DERIVATIVES

Reaction Scheme 5 discloses an exemplary synthetic route to the preparation of the compounds of the invention where the group designated W in Formula 1 is CRCO$_2$R. In accordance with this scheme a compound of Formula 9 is reacted with ethyl bromoacetate in the presence of zinc powder (Reformatsky reaction) to provide a tertiary alcohol (not shown in the scheme) that is dehydrated by treatment with Burgess reagent ($CH_3O_2CNSO_2N(C_2H_5)_3$) to give 1-aryl or 1-heteroaryl 4-(6-ethoxycarbonylmethylene-cyclohex-1-en-1-yl)-but-1-yn-3-ene derivatives of Formula 19. The compounds of Formula 19 can also be converted into further homologs and derivatives by reactions well known in the art.

The 2-[2-(trimethyl)silylethenyl]-2-cyclohexan-1-one derivatives of Formula 21 are then reacted with iodine in methylene chloride to provide 2-(2-iodoethenyl)-2-cyclohexan-1-one derivatives of Formula 22. The latter iodo compounds are then reacted with an ethynyl-aryl or ethynyl-heteroaryl reagent of the formula HC≡C—Y(R)—A—B to provide 1-aryl or 1-heteroaryl 4-(cyclohexane-1-one-2-yl)-but-1-yn-3-ene derivatives of Formula 23. The reagents

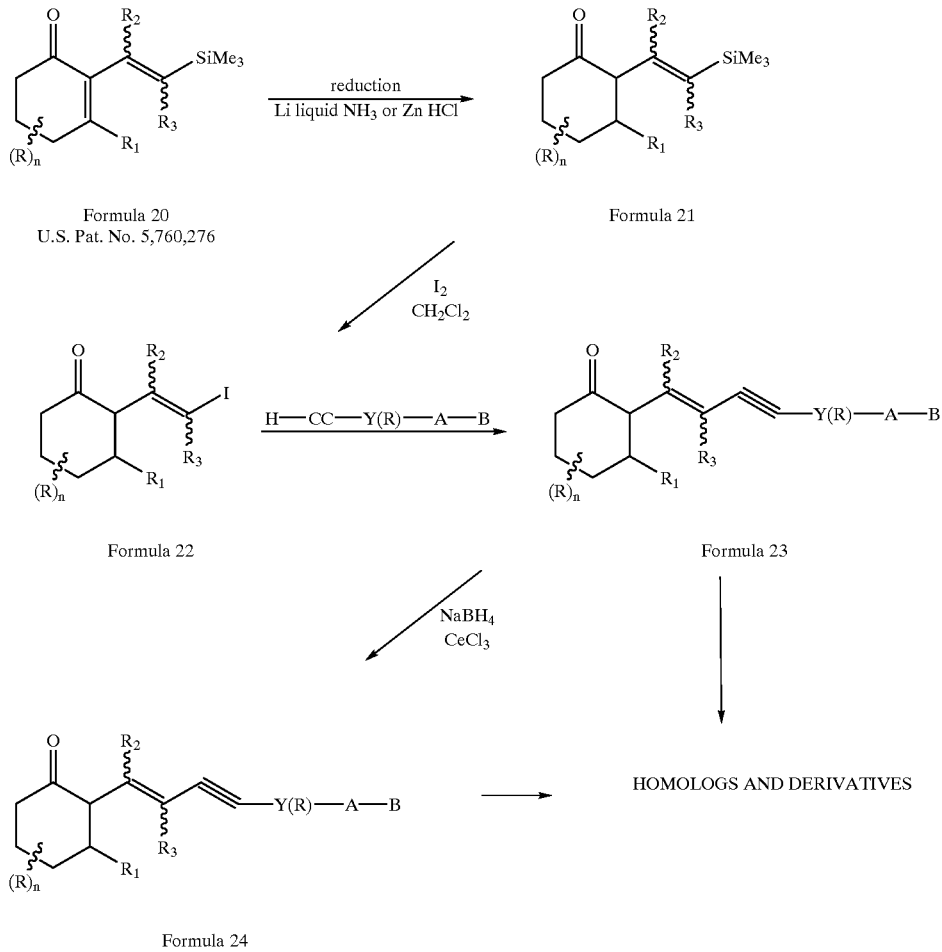

Reaction Scheme 6 describes an exemplary synthetic route to preparation of compounds of the invention in accordance with Formulas 2 and 4, that is compounds which are cyclohexane derivatives. The starting compound in this synthetic route is a 2-[2-(trimethyl)silylethenyl]-2-cyclohexen-1-one derivative of Formula 20 which can be obtained in accordance with the teachings of U.S. Pat. No. 5,760,276. The endocyclic double bond of the 2-[2-(trimethyl)silylethenyl]-2-cyclohexen-1-one derivative of Formula 20 is reduced with a reducing agent to provide a 2-[2-(trimethyl)silylethenyl]-2-cyclohexan-1-one derivative of Formula 21. Reducing agents which are generally known in the art to be suitable for the selective reduction of the double bond of enone compounds are, generally speaking, suitable for this reaction. Examples are lithium metal in liquid ammonia, or zinc in hydrochloric acid, as is indicated in the reaction scheme.

HC≡C—Y(R)—A—B can be obtained in accordance with the teachings of U.S. Pat. No. 5,760,276 and their reactions with the iodo compounds of Formula 22 are also conducted in accordance with the teachings disclosed in that patent. The compounds of Formula 23 are within the scope of Formula 2. The ketone function of the compounds of Formula 23 can be reduced with a suitable reagent, for example with sodium borohydride and cerium trichloride, to provide 1-aryl or 1-heteroaryl 4-(1-hydroxy-cyclohexane-2-yl)-but-1-yn-3-ene derivatives of Formula 24. The 1-aryl or 1-heteroaryl 4-(1-hydroxy-cyclohexane-2-yl)-but-1-yn-3-ene derivatives of Formula 24 are within the scope of Formula 4. The compounds of Formula 23 and of Formula 24, both, can be converted to further compounds of the invention as is indicated in the reaction scheme by the designation "homologs and derivatives."

REACTION SCHEME 7

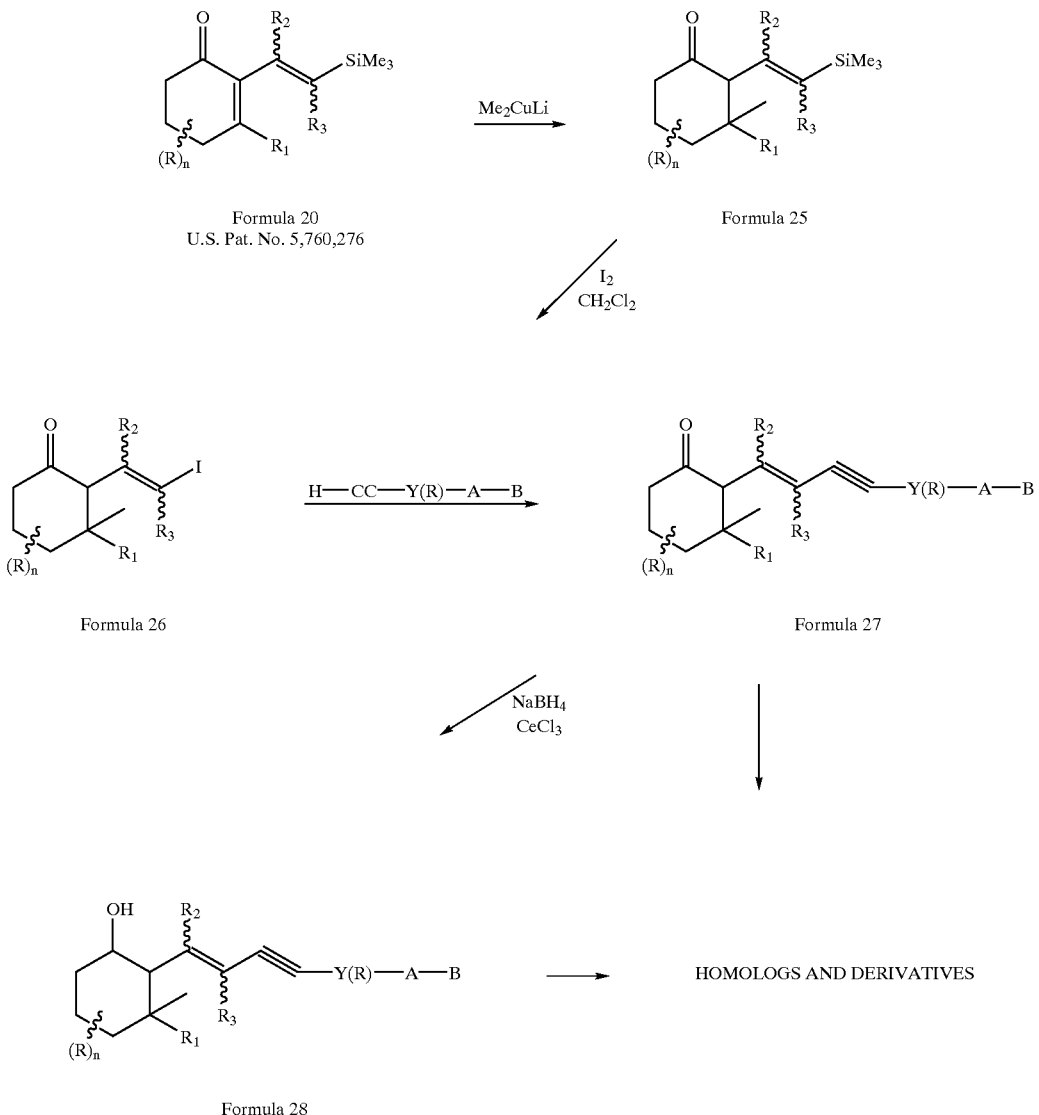

Formula 20
U.S. Pat. No. 5,760,276

Formula 25

Formula 26

Formula 27

Formula 28

HOMOLOGS AND DERIVATIVES

Referring now to Reaction Scheme 7 an exemplary synthetic route is disclosed for the preparation of preferred compounds of the invention wherein the cyclohexyl group has one, or preferably two methyl substituents on the carbon adjacent to the carbon linked to the ethenyl function. In accordance with this scheme the endocyclic double bond of a 2-[2-(trimethyl)silylethenyl]-2-cyclohexen-1-one derivative of Formula 20 (U.S. Pat. No. 5,760,276) is saturated by addition of a methyl group in a "cuprate addition" reaction, employing dimethyl-copper-lithium (($CH_3$)$_2$CuLi) reagent in the presence of (trimethyl)silyl chloride, in analogy to a similar reaction disclosed in U.S. Pat. No. 5,760,276. The product of this reaction is a 2-[2-(trimethyl)silylethenyl]-3-methyl-2-cyclohexan-1-one derivative of Formula 25. The compound of Formula 25 is reacted with iodine in methylene chloride to replace the (trimethyl)silyl group with iodine and to provide a 2-(2-iodoethenyl)-3-methyl-2-cyclohexan-1-one derivative of Formula 26. The compound of Formula 26 is reacted with the reagent HC≡C—Y(R)—A—B, as described above in connection with Reaction Scheme 6, to give 1-aryl or 1-heteroaryl 4-(3-methyl-cyclohexan-1-one-2-yl)-but-1-yn-3-ene derivatives of Formula 27, within the scope of general Formula 2. The 1-aryl or 1-heteroaryl 4-(3-methyl-cyclohexane-1-on-2-yl)-but-1-yn-3-ene derivatives of Formula 27 are reduced (for example with sodium borohydride and cerium trichloride) to yield 1-aryl or 1-heteroaryl 4-(-1-hydroxy-3-methyl-cyclohexan-2-yl)-but-1-yn-3-ene derivatives of Formula 28, within the scope of general Formula 4. The compounds of Formula 27 and of Formula 28 can be converted to further compounds of the invention, indicated in the reaction scheme as "homologs and derivatives".

REACTION SCHEME 8

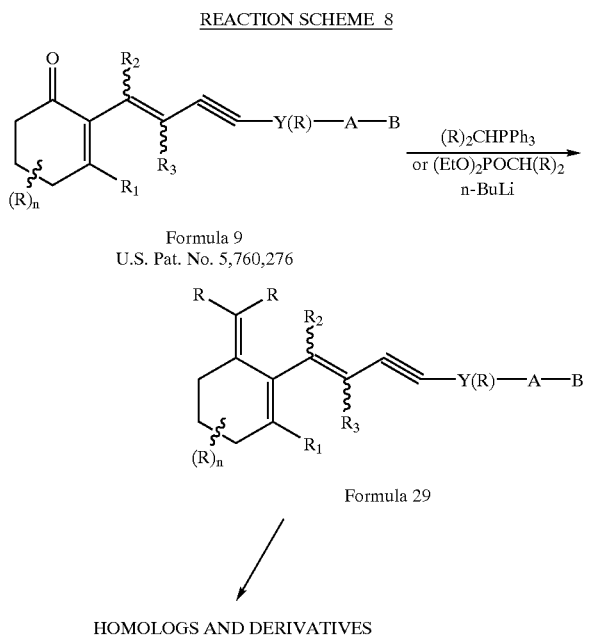

An exemplary process for preparing compounds of the invention where the W group of Formulas 1 and 2 is $C(R)_2$ is dislosed in Reaction Scheme 8. The symbol R is defined as in connection with Formulas 1 and 2. In accordance with this scheme, a 1-aryl or 1-heteroaryl 4-(cyclohex-2-en-1-on-2-yl)-but-1-yn-3-ene derivative of Formula 9 is reacted with a Wittig reagent of the formula $(R)_2CHPPh_3$ in the presence of strong base, such an n-butyl lithium. Instead of Wittig reagent, a Horner Emmons reagent of the formula $(EtO)_2POCH(R)_2$ can also be used under conditions normally employed for Horner Emmons reactions. The product of the Wittig or Horner Emmons reactions is a 1-aryl or 1-heteroaryl 4-(1-dialkyl or diaryl methylidene-cyclohex-2-en-2-yl)-but-1-yn-3-ene derivative of Formula 29 also within the scope of the present invention. The compounds of Formula 29 can be converted to further derivatives within the scope of the invention as is indicated in the reaction scheme by conversion to "homologs and derivatives".

REACTION SCHEME 9

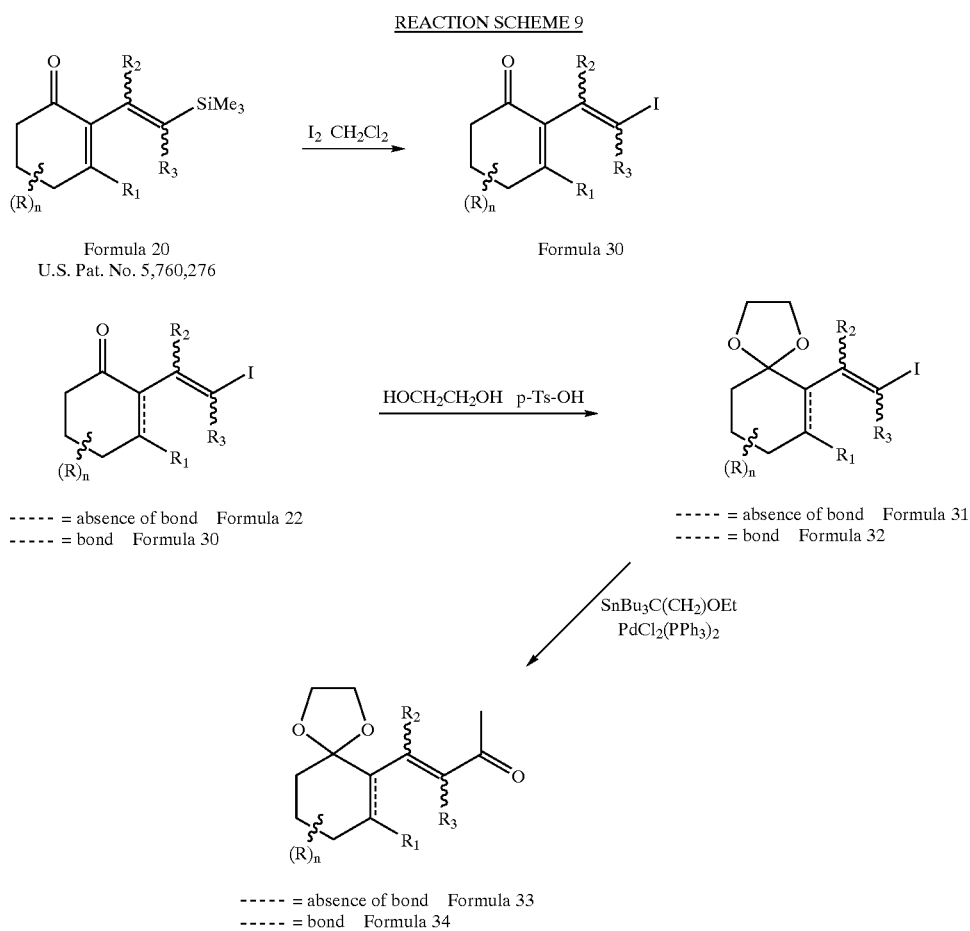

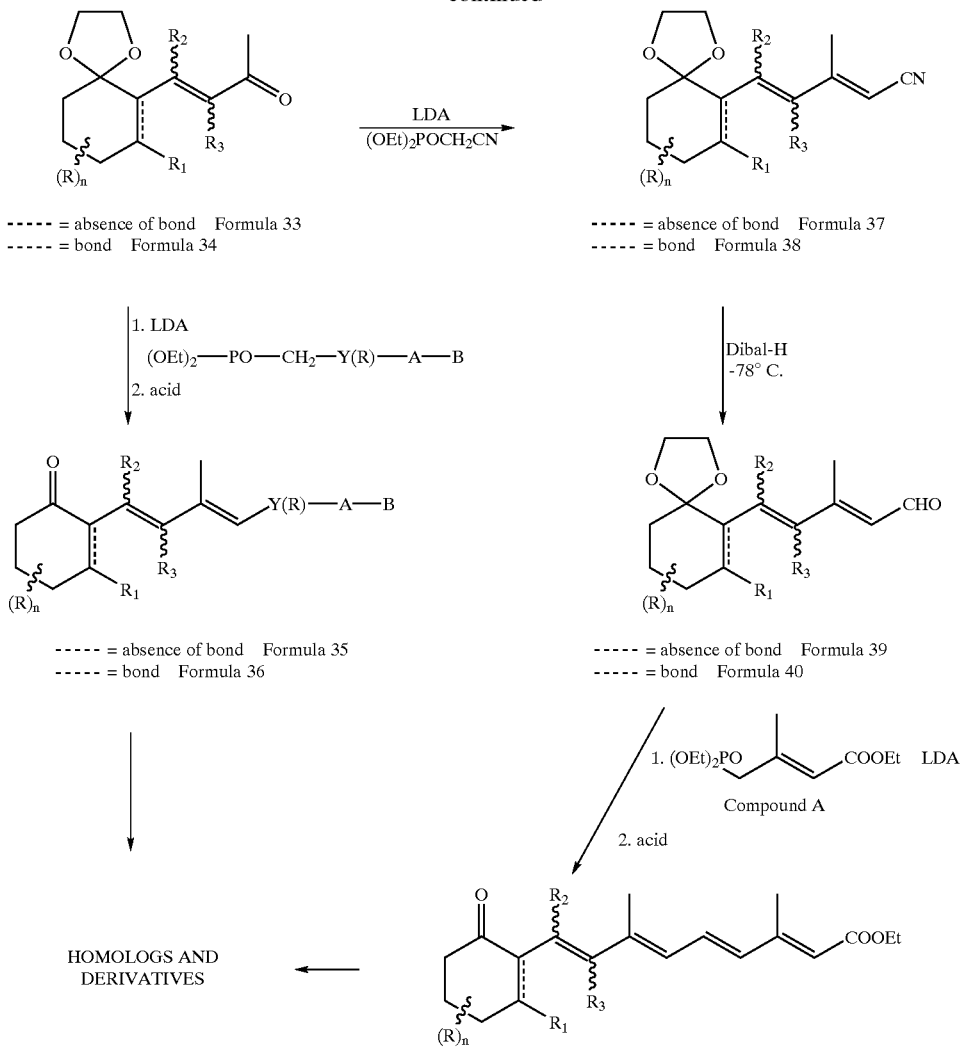

Reaction Scheme 9 discloses an exemplary synthetic route for preparation of compounds of the invention where the X group in Formula 1–4 is $(CR=CR)_{n'}$. The starting compounds in this scheme are 2-(2-4 iodoethenyl)-2-cyclohexan-1-one derivatives of Formula 22 (obtained as indicated in Reaction Scheme 6) and/or 2-(2-iodoethenyl)-2-cyclohexen-1-one derivatives of Formula 30 that can be prepared from 2-[2-(trimethyl)silylethenyl]-2-cyclohexen-1-one derivatives of Formula 20 by treatment with iodine in methylene chloride, as is indicated in this scheme. The ketone finction of the iodo compounds of Formula 22 and/or Formula 30 is then protected by conversion to a cyclic ketal by treatment with ethylene glycol in the presence of acid, to provide the dioxolane (ketal) derivatives of Formulas 31 and/or 32.

The protected dioxolane (ketal) derivatives of Formulas 31 and/or 32 are reacted with (1-ethoxyvinyl)tributyltin in the presence of bis(triphenylphosphine)palladium(II) chloride to introduce the acetyl group adjacent to the vinyl group and to yield the enone compounds of Formulas 33 and/or 34. The latter reaction is known in the art as a Stille coupling. (1-Ethoxyvinyl)tributyltin is available from Aldrich Chemical Co.) The enone compounds of Formula 33 and/or 34 are reacted with a Horner Emmons reagent of the formula $(EtO)_2$—PO—$CH_2$—Y(R)—A—B in the presence of strong base such as lithium diisopropylamide (LDA). The symbols Y, R, A and B for the reagent $(EtO)_2$—PO—$CH_2$—Y(R)—A—B are defined as in connection with Formulas 1–4. Examples for the reagents $(EtO)_2$—PO—$CH_2$—Y(R)—A—B are: ethyl [4-(diethoxyphosphinyl)methyl]benzoate, ethyl [6-(diethoxyphosphinyl)methyl]pyridine-3-carboxylate, ethyl [5-(diethoxyphosphinyl)methylfuran-2-carboxylate and ethyl [5-(diethoxyphosphinyl) methylthiophen-2-carboxylate. These reagents can be obtained in accordance with or in analogy to the process described in U.S. Pat. No. 5,455,265 for the synthesis of ethyl [4-2 (diethoxyphosphinyl)methyl]benzoate and ethyl [5-3 (diethoxyphosphinyl)methylfuran-2-carboxylate. The specification of U.S. Pat. No. 5,455,265 is incorporated herein by reference. The products of the Horner Emmons reaction with the reagent $(EtO)_2$—PO—$CH_2$—Y(R)—A—B are thereafter treated with acid to remove the dioxolane protective group and to provide the 1-aryl or 1-heteroaryl 4-(cyclohexan-1-on-2-yl or 4-(cyclohex-1-on-2-en-2-yl) butadiene derivatives of Formula 35 and/or Formula 36. The compounds of Formula 35 and Formula 36 are within the scope of the invention and can also be converted to further "homologs and derivatives" within the scope of the invention.

Referring still to Reaction Scheme 9, the enone compounds of Formula 33 and/or 34 can also be reacted in a Horner Emmons reaction, in the presence of strong base (lithium diisopropylamide, LDA) with diethyl cyanomethylphosphonate. The latter reagent is commercially available. The products of this Horner Emmons reaction are 4-(cyclohexen-yl or cyclohexan-yl)-1-cyano-2-methyl-butadiene derivatives of Formulas 37 and/or 38 in which the endocyclic ketone is still protected as a cyclic ketal. Those skilled in the art will readily understand that instead of a Horner Emmons reaction the compounds of Formulas 37 and/or 38 can also be obtained as a result of analogous Wittig reactions. The cyano function of the compounds of Formulas 37 and/or 38 is reduced by treatment with a mild reducing agent, such as diisobutylaluminum hydride (Dibal-H) to provide the aldehyde compounds of Formula 39 and/or Formula 40. Another Horner Emmons reaction performed on the aldehydes of Formula 39 and/or Formula 40 with the reagent diethyl(E)-3-carboethoxy-2-methyl-1-allylphosphonate (Compound A) in the presence of strong base (LDA) provides, after removal of the cyclic ketal protective group, the 1-ethoxycarbonyl-6-(cyclohexan-1-one-2-yl or 6-(cyclohex-1-one-2-en-2-yl)-hexatriene derivatives of Formula 41 and/or Formula 42.

The compounds of Formulas 41 and 42 are within the scope of the present invention and can be converted into further compounds also within the scope of the invention by reactions such as saponification, amide formation, reduction to the aldehyde or alcohol stage, and the like. This is indicated in the reaction scheme by conversion to "homologs and derivatives".

The reagent diethyl(E)-3-carboethoxy-2-methyl-1-allylphosphonate (Compound A) is obtained in a sequence of reactions starting from the commercially available ethyl (Z)-3-formyl-2-butenoate (Compound B). In this preparation the aldehyde function of Compound B is reduced with sodium borohydride, and the resulting primary alcohol is reacted with phosphorous tribromide. The resulting ethyl (Z)-3-bromo-2-butenoate (Compound C) is reacted with triethyl phosphonate to give Compound A.

REACTION SCHEME 10

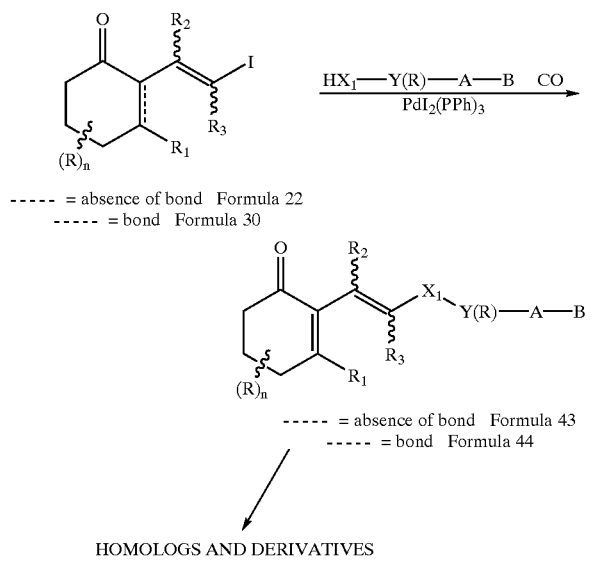

$X_1$ = O, S or NH

Reaction Scheme 10 discloses examples for processes to obtain compounds of the invention where with reference to Formulas 1–4 the X group is C(O)O, C(O)S, CONR, or CSNR. These compounds of the invention can be made by reacting the 2-(2-iodoethenyl)-2-cyclohexan-1-one derivatives of Formula 22 (obtained as indicated in Reaction Scheme 6) and/or 2-(2-iodoethenyl)-2-cyclohexen-1-one derivatives of Formula 30 (obtained as indicated in Reaction Scheme 9) with a reagent of the formula $HX_1$—Y(R)—A—B and carbon monoxide (CO) in the presence of tris (triphenylphosphine)palladium(II) iodide catalyst in analogy to the reactions described in the treatise Heck, Richard F. "Palladium Reagents in Organic Synthesis" Academic Press (Orlando Fla.) 1985, pp 374–381, incorporated herein by reference. The symbol $X_1$ in the formula of the reagent $HX_1$—Y(R)—A—B represents O, S, or NH, thus the reagents are hydroxyl, thiol or primary amine derivatives of aryl and heteroaryl compounds. Examples for these reagents are ethyl 4-hydroxybenzoate, ethyl 4-mercaptobenzoate, ethyl 4-aminobenzoate, ethyl 6-hydroxynicotinoate, ethyl 6-aminonicotinoate, ethyl 5-hydroxyfuran-2-carboxylate, ethyl 5-aminofuran-2-carboxylate, ethyl 5-hydroxythiophen-2-carboxylate and ethyl 5-aminothiophen-2-carboxylate. The resulting compounds of Formula 43 and 44 are within the scope of the invention and can be converted to further "homologs and derivatives".

SPECIFIC EXAMPLES (Trimethylsilyl)ethyl 4-Ethynylbenzoate
(Compound C)

A solution of (trimethylsilyl)ethyl 4-iodobenzoate (2.5 g, 7.2 mmol), (tributyltin)acetylene (2.5 mL, 8.6 mmol) and THF (50 mL) was purged with argon for 10 min, and then treated with bis(triphenylphosphine)palladium (II) chloride (126 mg, 0.18 mmol). The suspension was stirred overnight at room temperature and then for 1 hour at 50 °C. The solution was treated with $NH_4Cl$ and the product extracted with 50% ethyl acetate and hexane solution. The layers were separated and the aqueous layer extracted twice more with the same organic solution. The combined organic layers were washed with brine, and dried ($MgSO_4$), and filtered and the solvents were removed under reduced pressure. The residue was purified by silica gel chromatography (98:2, hexane:ethyl acetate) to give the title compound as a yellow oil.

PNMR (300 MHz, $CDCl_3$) δ 0.08 (s, 9 H), 1.13 (t, 2 H, J=8.5 Hz), 3.21 (s, 1 H), 4.17 (t, 2 H, J=8.5 Hz), 7.54 (d, 2 H, J=8.3 Hz), 7.99 (d, 2 H, J=8.3 Hz).

(Trimethylsilyl)ethyl 4-(4-(2-Methyl-6-oxocyclohex-1-enyl)but-3-en-1ynl)benzoate
(Compound D)

A solution of 1-iodo-2-(2-methyl-6-oxocyclohex-1-enyl) ethene (Compound E, available in accordance with the teachings of U.S. Pat. No. 5,760,276, 0.70 g, 2.67 mmol), (trimethylsilyl)ethyl 4-ethynylbenzoate (Compound C, 0.79 g, 3.21 mmol) and triethylamine (32 mL) was purged with argon for 10 minutes, and then treated with bis (triphenylphosphine)palladium (II) chloride (47 mg, 0.07 mmol) and copper (I) iodide (12.8 mg, 0.07 mmol). The solution was sti rre d 40° C. for 3 hours, and concentrated under a water aspirator vacuum. The residue was dissolved in ethyl acetate and washed with saturated aqueous $NH_4Cl$. The layers were separated and the aqueous layer was extracted twice with ethyl acetate. The combined organic fractions were washed with water, and brine, and dried ($MgSO_4$). The solvents were removed under reduced pressure, and the residue was purified by silica gel chromatography (90:10, hexane:ethyl acetate) to give the title compound.

PNMR (300 MHz, CDCl$_3$) δ 0.08 (s, 9 H), 1.13 (t, 2 H, J=8.5 Hz), 1.97 (m, 2 H), 2.10 (s, 3 H), 2.47 (m, 4 H), 4.41 (t, 2 H, J=8.5 Hz), 6.40 (d, 1 H, J=15 Hz), 6.84 (d, 1 H, J=15 Hz), 7.49 (d, 2 H, J=8.3 Hz), 7.97 (d, 2 H, J=8.3 Hz).

Ethyl (+)-(E)-4-(4-(6-Hydroxy-2-methylcyclohex-1-enyl)but-3-en-1-ynyl)benzoate (Compound 1); Ethyl (−)-(E)-4-(4-(6-Hydroxy-2-methylcyclohex-1-enyl)but-3-en-1-ynyl)benzoate (Compound 1a) and Ethyl (+)-(E)-4-(4-(6-Hydroxy-2-methylcyclohex-1-enyl)but-3-en-1-ynyl)benzoate (Compound 1b)

Cerium trichloride heptahydrate (3.63 g, 9.73 mmol) and ethyl 4-(4-(2-methyl-6-oxocyclohexen-1-yl)but-3-en-1-ynyl)benzoate (Compound F, available in accordance with the teachings of U.S. Pat. No. 5,760,276, 300 mg, 0.973 mmol) were dissolved in methanol (60 mL) and treated with sodium borohydride (368 mg, 9.73 mmol). The resulting solution was stirred in the dark for 1 hour at 0° C. The excess hydride was quenched by the addition of 10% aqueous HCl and the products extracted 3 times with ethyl acetate. The combined organic layers were washed with water, and brine, and dried (MgSO4), and filtered and the solvents were removed in vacuo. The residue was purified by silica gel chromatography using a solution of hexane and ethyl acetate in a 5 to 1 ratio, respectively, to give the racemic title compound as a colorless oil. The (−) and (+) enantiomers were separated by chiral stationary phase high pressure liquid chromatography (HPLC) using a 1 cm by 25 cm Chiracel-OD column using an eluent of 5% isopropyl alcohol in hexane at a flow rate of 2.75 mL/min. The (−) isomer had a specific rotation ([α]$_D$) of −24.2 (EtOAc) and the (+) isomer had a [α]$_D$ of +24.4 (EtOAc). The absolute stereochemistry was not determined.

PNMR (500 MHz, CDCl$_3$) δ 1.39 (t, 3 H, J=7.0 Hz), 1.63 (m, 2 H), 1.91 (m, 1 H), 1.87 (s, 3 H), 1.93 (m, 1 H), 2.17 (m, 2 H), 4.39 (q, 2 H, J=7.0 Hz), 6.10 (d, 1 H, J=16 Hz), 7.12 (d, 1 H, J=16 Hz), 7.49 (dd, 2 H, J=6.5, 1.5 Hz), 7.99 (dd, 2 H, J=6.5, 1.5 Hz).

(Trimethylsilyl)ethyl (+)-(E)-4-(4-(6-Hydroxy-2-methylcyclohex-1-enyl)but-3-en-1-ynyl)benzoate (Compound 2).

Cerium trichloride heptahydrate (4.88 g, 13.1 mmol) and (trimethylsilyl)ethyl 4-(4-(2-methyl-6-oxocyclohexen-1-yl)but-3-en-1-ynyl)benzoate (Compound D, 500 mg, 1.31 mmol) were dissolved in ethanol (80 mL), cooled to 0° C. and treated with sodium borohydride (495 mg, 13.1 mmol) in three equal portions. The resulting solution was stirred in the dark for 20 minutes at 0° C. The excess hydride was quenched by the addition of saturated aqueous NH$_4$Cl and the mixture was extracted 3 times with ethyl acetate. The combined organic layers were washed with water, and brine, dried (MgSO$_4$), filtered and the solvents were removed in vacuo. The residue was purified by silica gel chromatography using a solution of hexane and ethyl acetate in a 5 to 1 ratio, respectively, to give the racemic title compound as a yellow oil.

PNMR (300 MHz, acetone-d$_6$) δ 0.09 (s, 9 H), 1.14 (m, 2 H), 1.57 (m, 2 H) 1.84 (s, 3 H), 1.86 (m, 2 H), 2.13 (m, 2 H), 4.40 (s, 1 H), 4.41 (m, 2 H), 6.16 (d, 1 H, J=16 Hz), 7.13 (d, 1 H, J=16 Hz), 7.54 (dd, 2 H, J=6.5, 1.5 Hz), 7.98 (dd, 2 H, J=6.5, 1.5 Hz).

Ethyl (−)-(E)-4-(4-(6-Acetyloxy-2-methylcyclohex-1-enyl)but-3-en-1-ynyl)benzoate (Compound 3a)

General Procedure A

Ethyl (−)-(E)-4-(4-(6-hydroxy-2-methylcyclohex-1-enyl)but-3-en-1-ynyl)benzoate (Compound 1a, 50 mg, 0.161 mmol) was dissolved in dichloromethane (2 mL) and treated with pyridine (0.039 mL, 0.48 mmol) and acetic anhydride (0.031 mL, 0.32 mmol). The solution was protected from light and stirred for 30 hours at room temperature. The solution was diluted with ethyl acetate and 10% aqueous HCl was added. The layers were separated and the aqueous layer was extracted 2 times with ethyl acetate. The combined organic layers were washed with water, and brine, dried (MgSO$_4$), filtered and the solvents were removed in vacuo. The residue was purified by silica gel chromatography using a solution of hexane and ethyl acetate in a 95 to 5 ratio, respectively, to give the title compound as a colorless oil. [α]$_D$=−110.7 (EtOAc), PNMR (300 MHz, CDCl$_3$) δ 1.32 (t, 3 H, J=7.1 Hz), 1.59 (m, 3 H), 1.85 (s, 3 H), 1.93 (m, 1 H), 2.00 (s, 3 H), 2.16 (m, 2 H), 4.30 (q, 2 H, J=7.1 Hz), 5.61 (s, 1 H), 5.63 (d, 1 H, J=16 Hz), 7.01 (d, 1 H, J=16 Hz), 7.41 (d, 2 H, J=8.4 Hz), 7.99 (d, 2 H, J=8.4 Hz).

Ethyl (+)-(E)-4-(4-(6-Acetyloxy-2-methylcyclohex-1-enyl)but3-en-1-ynyl)benzoate (Compound 3b)

The title compound, a colorless oil, was prepared from ethyl (+)-(E)-4-(4-(6-hydroxy-2-methylcyclohex-1-enyl)but-3-en-1-yn-yl)benzoate (Compound 1b, 50 mg, 0.161 mmol) as described in General Procedure A.

[α]$_D$=+109.5 (EtOAc), PNMR (300 MHz, CDCl$_3$) δ 1.32 (t, 3 H, J=7.1 Hz), 1.59 (m, 3 H), 1.85 (s, 3 H), 1.93 (m, 1 H), 2.00 (s, 3 H), 2.16 (m, 2 H), 4.30 (q, 2 H, J=7.1 Hz), 5.61 (s, 1 H), 5.63 (d, 1 H, J=16 Hz), 7.01 (d, 1 H, J=16 Hz), 7.41 (d, 2 H, J=8.4 Hz), 7.99 (d, 2 H, J=8.4 Hz).

Ethyl (−)-(E)-4-(4-(6-Propionyloxy-2-methylcyclohex-1-enyl)but-3-en-1-ynyl)benzoate (Compound 4a)

General Procedure B.

Ethyl (−)-(E)-4-(4-(6-hydroxy-2-methylcyclohex-1-enyl)but-3-en-1-ynyl)benzoate (Compound 1a, 25 mg, 0.081 mmol) was dissolved in dichloromethane (1 mL) and treated with pyridine (0.25 mL , 3.07 mmol) and the reaction mixture was cooled to 0° C. Propionyl chloride (0.070 mL, 0.81 mmol) and 3 mg of dimethylaminopyridine (DMAP) was added and the solution was protected from light and stirred for 36 hours at room temperature. The solution was diluted with ethyl ether and 10% aqueous HCl was added. The layers were separated and the aqueous layer was extracted 2 times with ethyl ether. The combined organic layers were washed with 5% aqueous sodium bicarbonate, and brine, dried (K$_2$CO$_3$), filtered and the solvents were removed in vacuo. The residue was purified by silica gel chromatography using a solution of hexane and ethyl acetate in a 95 to 5 ratio, respectively, to give the title compound as a colorless oil. [α]$_D$=−124 (EtOAc), PNMR (300 MHz, CDCl$_3$) δ 1.16 (t, 3 H, J=7.7 Hz), 1.39 (t, 3 H, J=7.1 Hz), 1.67 (m, 3 H), 1.92 (s, 3 H), 1.97 (m, 1 H), 2.22 (m, 2 H), 2.34 (q, 2 H, J=7.7 Hz), 4.37 (q, 2 H, J=7.1 Hz), 5.68 (s, 1 H), 5.69 (d, 1 H, J=16 Hz), 7.08 (d 1 H, J=16 Hz), 7.47 (d, 2 H, J=8.5 Hz), 7.98 (d, 2 H, J=8.5 Hz).

Ethyl (+)-(E)-4-(4-(6-Propionyloxy-2-methylcyclohex-1-enyl)but-3-en-1-ynyl)benzoate (Compound 4b)

The title compound, a colorless oil, was prepared from ethyl (+)-(E)-4-(4-(6-hydroxy-2-methylcyclohex-1-enyl)

but-3-en-1-ynyl)benzoate (Compound 1b, 50 mg, 0.161 mmol) as described in General Procedure B.

$[\alpha]_D$=+129 (EtOAc), PNMR (300 MHz, CDCl$_3$) δ 1.16 (t, 3 H, J=7.7 Hz), 1.39 (t, 3 H, J=7.1 Hz), 1.67 (m, 3 H), 1.92 (s, 3 H), 1.97 (m, 1 H), 2.22 (m, 2 H), 2.34 (q, 2 H, J=7.7 Hz), 4.37 (q, 2 H, J=7.1 Hz), 5.68 (s, 1 H), 5.69 (d, 1 H, J=16 Hz, 7.08 (d, 1 H, J=16 Hz), 7.47 (d, 2 H, J=8.5 Hz), 7.98 (d, 2 H,J=8.5 Hz).

Ethyl (−)-(E)-4-(4-(6-iso-Butyryloxy-2-methylcyclohex-1-enyl)but-3-ene-1-ynyl)benzoate (Compound 5a)

General Procedure C.

Ethyl (−)-(E)-4-(4-(6-hydroxy-2-methylcyclohex-1-enyl)but-3-en-1-ynyl)benzoate (Compound 1a, 25 mg, 0.081 mmol) was dissolved in dichloromethane (1 mL) and treated with pyridine (0.26 mL, 3.22 mmol) and cooled to 0° C. iso-Butyryl chloride (0.084 mL, 0.81 mmol) and the solution was protected from light and stirred for 48 hours at room temperature. The solution was diluted with ethyl acetate and saturated aqueous NH$_4$Cl was added. The layers were separated and the aqueous layer was extracted twice with ethyl acetate. The combined organic layers were washed with brine, dried (Na$_2$SO$_4$), filtered and the solvents were removed in vacuo. The residue was purified by silica gel chromatography using a solution of hexane and ethyl acetate in a 95 to 5 ratio, respectively, to give the title compound as a colorless oil. $[\alpha]_D$=−130 (EtOAc), PNMR (300 MHz, CDCl$_3$) δ 1.17 (d, 6 H, J=7.7 Hz), 1.39 (t, 3 H, J=7.1 Hz), 1.67 (m, 3 H), 1.92 (s, 3 H), 1.96 (m, 1 H), 2.21 (m, 2 H), 2.54 (m, 1 H, J=7.7 Hz), 4.3 7 (q, 2 H, J=7.1 Hz), 5.66 (s, 1 H), 5.67 (d, 1 H, J=16 Hz), 7.08 (d, 1 H, J=16 Hz), 7.48 (d, 2 H, J=8.3 Hz), 7.98 (d, 2 H, J=8.3 Hz).

Ethyl (+)-(E)-4-(4-(6-iso-Butyryloxy-2-methyicyclohex-1-enyl)but-3-ene-1-ynyl)benzoate (Compound 5b)

The title compound, a colorless oil, was prepared from ethyl (+)-(E)-4-(4-(6-hydroxy-2-methylcyclohex-1-enyl)but-3-en-1-ynyl)benzoate (Compound 1b, 25 mg, 0.081 mmol) and iso-butyryl chloride (0.084 mL, 0.81 mmol) as described in General Procedure C. $[\alpha]_D$=+138 (EtOAc), PNMR (300 MHz, CDCl$_3$) δ 1.17 (d, 6 H, J=7.7 Hz), 1.39 (t, 3 H, J=7.1 Hz), 1.67 (m, 3 H), 1.92 (s, 3 H), 1.96 (m, 1 H), 2.21 (m, 2 H), 2.54 (m, 1 H, J=7.7 Hz), 4.3 7 (q, 2 H, J=7.1 Hz), 5.66 (s, 1 H), 5.67 (d, 1 H, J=16 Hz), 7.0 8 (d, 1 H, J=16 Hz), 7.48 (d, 2 H, J=8.3 Hz), 7.98 (d, 2 H, J=8.3 Hz).

Ethyl (−)-(E)-4-(4-(6-(2,2-Dimethylpropanoyl)oxy-2-methylcyclohex-1-enyl)but-3-ene-1-ynyl)benzoate (Compound 6a)

General Procedure D

Ethyl (−)-E-4-(4(6-hydroxy-2-methylcyclohex-1-enyl)but-3-en-1-ynyl)benzoate (Compound 1a, 30 mg, 0.097 mmol) was dissolved in dichloromethane (1.5 mL) and treated with triethylamine (0.081 mL, 0.58 mmol) and cooled to 0° C. 2,2-Dimethylpropanoyl chloride (0.043 mL, 0.35 mmol) and 3 mg of dimethylaminopyridine (DMAP) were added and the solution was protected from light and stirred for 48 hours at room temperature. The solution was diluted with ethyl acetate and saturated aqueous NH$_4$Cl was added. The layers were separated and the aqueous layer was extracted twice with ethyl acetate. The combined organic layers were washed with brine, dried (Na$_2$SO$_4$), filtered and the solvents were removed in vacuo. The residue was purified by silica gel chromatography using a solution of hexane and ethyl acetate in a 95 to 5 ratio, respectively, to give the title compound as a colorless oil. $[\alpha]_D$=−141 (EtOAc), PNMR (300 MHz, CDCl$_3$) δ 1.20 (s, 9 H), 1.39 (t, 3 H, J=7.1 Hz), 1.66 (m, 3 H), 1.88 (m, 1 H), 1.92 (s, 3 H), 2.21 (m, 2 H), 2.54 (m, 1 H, J=7.7 Hz), 4.37 (q, 2 H, J=7.1 Hz), 5.62 (s, 1 H), 5.63 (d, 1 H, J=16 Hz), 7.07 (d, 1 H, J=16 Hz), 7.47 (dd, 2 H, J=6.7, 1.7 Hz), 7.97 (dd, 2 H, J=6.7, 1.7 Hz).

Ethyl (+)-(E)-4-(4-(6-(2,2-Dimethylpropanoyl)oxy-2-methylcyclohex-1-enyl)but-3-ene-1-ynyl)benzoate (Compound 6b)

The title compound, a colorless oil, was prepared from ethyl (+)-(E)-4-(4-(6-hydroxy-2-methylcyclohex-1-enyl)but-3-en-1-ynyl)benzoate (Compound 1b, 30 mg, 0.097 mmol) and tert-butyryl chloride (0.043 mL, 0.35 mmol) as described in General Procedure D. $[\alpha]_D$=+141 (EtOAc), PNMR (300 MHz, CDCl$_3$) δ 1.20 (s, 9 H), 1.39 (t, 3 H, J=7.1 Hz), 1.66 (m, 3 H), 1.88 (m, 1 H), 1.92 (s, 3 H), 2.21 (m, 2 H), 2.54 (m, 1 H, J=7.7 Hz), 4.37 (q, 2 H, J=7.1 Hz), 5.62 (s, 1 H), 5.63 (d, 1 H, J=16 Hz), 7.07 (d, 1 H, J=16 Hz), 7.47 (dd, 2 H,J=6.7, 1.7 Hz), 7.97 (dd, 2 H, J=6.7, 1.7 Hz).

Ethyl (−)-(E)-4-(4-(6-Benzoyloxy-2-methylcyclohex-1-enyl)but-3-ene-1-ynyl)benzoate (Compound 7a)

The title compound, a colorless oil, was prepared from ethyl (−)-(E)-4-(4-(6-hydroxy-2-methylcyclohex-1-enyl)but-3-en-1-ynyl)benzoate (Compound 1a, 30 mg, 0.097 mmol) and benzoyl chloride (0.041 mL, 0.35 mmol) as described in General Procedure D. $[\alpha]_D$=−100 (EtOAc), PNMR (300 MHz, CDCl$_3$) δ 1.37 (t, 3 H, J=7.1 Hz), 1.66 (m, 3 H), 1.97 (s, 3 H), 2.10 (m, 1 H), 2.28 (m, 2 H), 4.36 (q, 2 H, J=7.1 Hz), 5.78 (d, 1 H, J=16 Hz), 5.92 (s, 1 H), 7.41–7.45 (several ds, 4 H), 7.54 (m, 1 H), 7.95 (dd, 2 H, J=8.4, 1.8 Hz), 8.05 (dd, 2 H, J=8.6, 1.5 Hz).

Ethyl (+)-(E)-4-(4-(6-Benzoyloxy-2-methylcyclohex-1-enyl)but-3-en-1-ynyl)benzoate (Compound 7b)

The title compound, a colorless oil, was prepared from ethyl (+)-(E)-4-(4-(6-hydroxy-2-methylcyclohex-1-enyl)but-3-en-1-ynyl)benzoate (Compound 1b, 30 mg, 0.097 mmol) and benzoyl chloride (0.041 mL, 0.35 mmol) as described in General Procedure D. $[\alpha]_D$=+97 (EtOAc), PNMR (300 MHz, CDCl$_3$) δ 1.37 (t, 3 H, J=7.1 Hz), 1.66 (m, 3 H), 1.97 (s, 3 H), 2.10(m, 1 H), 2.28 (m,2 H),4.36 (q, 2 H, J=7.1 Hz), 5.78 (d, 1 H, J=16 Hz), 5.92 (s, 1 H), 7.41–7.45 (several ds, 4 H), 7.54 (m, 1 H), 7.95 (dd, 2 H, J=8.4, 1.8 Hz), 8.05 (dd, 2 H, J=8.6, 1.5 Hz). (Trimethylsilyl)ethyl (−)-(E)-4-(4-(6-Hydroxy-2-methylcyclohex-1-enyl)but-3-en-1-ynyl)benzoate (Compound 2a) and (Trimethylsilyl)ethyl (+)-(E)-4-(4-(6-Acetoxy-2-methylcyclohex-1-enyl)but-3-en-1-ynyl) benzoate (Compound 8b).

A suspension of (trimethylsilyl)ethyl (+)-(E)-4-(4-(6-hydroxy-2-methylcyclohex-1-enyl)but-3-en-1-ynyl) benzoate (Compound 2, 400 mg, 1.05 mmol), vinyl acetate (0.484 mL, 5.25 mmol), t-butyl methyl ether (13 mL) and 50 mg of ChiroCLEC-PC (Altus, Inc., Cambridge, Mass.) catalyst was stirred in the dark for 6 days at room temperature. The catalyst was removed by filtration and the filtrate concentrated under reduced pressure. The residue was subjected to silica gel chromatography (9:1::hexane:ethyl acetate) to give alcohol 4 and the acetate, (Compound 8), as a 93:7 mixture of enantiomers which were separated by recrystalization of its carboxylic acid derivative. The alcohol (Compound 2a) was purified to optical purity by chiral stationary phase high pressure liquid chromatography (HPLC) on a 1 cm by 25 cm Chiracel-OD column using an eluent of 5% isopropyl alcohol in hexane at a flow rate of 2.75 mL/min.

PNMR (300 MHz, acetone-$d_6$) δ 0.09 (s, 9 H), 1.14 (m, 2 H), 1.57 (m, 2 H) 1.84 (s, 3 H), 1.86 (m, 2 H), 2.13 (m, 2 H), 4.40 (s, 1 H), 4.41 (m, 2 H), 6.16 (d, 1 H, J=16 Hz), 7.13 (d, 1 H, J=16 Hz), 7.54 (dd, 2 H, J=6.5, 1.5 Hz), 7.98 (dd,2 H, J=6.5, 1.5 Hz).

(Trimethylsilyl)ethyl (−)-(E)-4-(4-(6-Acetyloxy-2-methylcyclohex-1-enyl)but-3-en-1-ynyl)benzoate
(Compound 8a)

The title compound, a colorless oil, was prepared from (trimethylsilyl)ethyl (−)-(E)-4-(4-(6-hydroxy-2-methylcyclohex-1-enyl)but-3-en-1-ynyl)benzoate (Compound 2a, 136 mg, 0.356 mmol) as described in General Procedure A. $[\alpha]_D$=−134 (EtOAc), PNMR (300 MHz, CDCl$_3$) δ 0.08 (s, 9 H), 1.13 (m, 2 H), 1.67 (m, 3 H) 1.92 (s, 3 H), 1.97 (m, 1 H), 2.08 (s, 3 H), 2.22 (m, 2 H), 4.41 (m, 2 H), 5.68 (s, 1 H), 5.70 (d, 1 H, J=16 Hz), 7.08 (d, 1 H, J=16 Hz), 7.47 (d, 2 H, J=8.5 Hz), 7.97 (d, 2 H, J=8.5 Hz).

(−)-(E)-4-(4-(6-Acetyloxy-2-methylcyclohex-1-enyl) but3-en-1-ynyl)benzoic Acid (Compound 9a)
General Procedure E.

(Trimethylsilyl)ethyl (−)-(E)-4-(4-(6-acetyloxy-2-methylcyclohex-1-enyl)but-3-en-1-ynyl)benzoate (Compound 8a, 50 mg, 0.118 mmol) was dissolved in DMSO (2 mL) and triethylammonium fluoride hydrate (50 mg, 0.335 mmol) was added. The solution was stirred for 1 hour at room temperature. The resulting yellow solution was poured into a separatory funnel containing 10 mL of 0.2 M HCl and 25 mL of ethyl acetate. The layers were separated and the aqueous layer was extracted twice with ethyl acetate. The combined organic layers were washed with water, and brine, and dried (MgSO$_4$). The filtered solvents were concentrated under reduced pressure and the solid residue was recrystalized from acetonitrile to give the title compound as a yellow crystalline solid. $[\alpha]_D$=−168 (EtOAc), PNMR (300 MHz, CDCl$_3$) δ 1.67 (m, 2 H) 1.92 (s, 3 H), 1.90 (m, 1 H), 2.01 (s, 3 H), 2.04 (m, 1 H), 2.24 (m, 2 H), 5.62 (s, 1 H), 5.69 (d, 1 H, J=16 Hz), 7.13 (d, 1 H, J=16 Hz), 7.54 (d, 2 H, J=8.4 Hz), 8.00 (d, 2 H, J=8.4 Hz).

(+)-(E)-4-(4-(6-Acetyloxy-2-methylcyclohex-1-enyl) but-3-en-1-ynyl)benzoic Acid (Compound 9b).

The title compound, a crystaline solid, was prepared from (trimethylsilyl)ethyl (+)-(E)-4-(4-(6-acetoxy-2-methylcyclohex-1-enyl)but-3-en-1-ynyl)benzoate (Compound 8b, 50 mg, 0.161 mmol) as described in General Procedure E. $[\alpha]_D$=+158 (EtOAc), PNMR (300 MHz, CDCl$_3$) δ 1.67 (m, 2 H) 1.92 (s, 3 H), 1.90 (m, 1 H), 2.01 (s, 3 H), 2.04 (m, 1 H), 2.24 (m, 2 H), 5.62 (s, 1 H), 5.69 (d, 1 H, J=16 Hz), 7.13 (d, 1 H, J=16 Hz), 7.54 (d, 2 H, J=8.4 Hz), 8.00 (d, 2 H, J=8.4 Hz).

Ethyl 4-(4-(6-Methoxyimino-2-methylcyclohex-1-enyl)but-3-en-1-ynyl)-3-eneynyl)benzoate
(Compound 10)

Ethyl 4-(4-(2-Methyl-6-oxocyclohexen-1-yl)but-3-en-1-ynyl)benzoate (Compound F, 150 mg, 0.486 mmol) was dissolved in ethanol (15 mL) and treated with methoxylamine hydrochloride (400 mg, 4.86 mmol) and sodium acetate trihydrate (992 mg, 7.29 mmol). The resulting solution was stirred for 80 hours at room temperature. The solution was concentrated in vacuo, diluted with saturated ammonium chloride, and the products were extracted 3 times with ethyl ether. The combined organic layers were washed with water, brine, dried (MgSO$_4$), filtered, and the solvents were removed in vacuo to give a yellow oily residue. The residue was purified by silica gel chromatography using a solution of hexane and ethyl acetate in a 5 to 1 ratio, respectively, to give the title compound as a yellow solid.

PNMR (300 MHz, CDCl$_3$) δ 1.40 (t, 3 H, J=7.1 Hz), 1.69 (m, 2 H, J=6.2 Hz), 2.01 (s, 3 H), 2.24 (t, 2 H, J=6.2 Hz), 2.58 (t, 2 H, J=6.4 Hz), 3.91 (s, 3 H), 4.38 (q, 2 H, J=7.1 Hz), 6.33 (d, 1 H, J=16 Hz), 6.95 (d, 1 H, J=16 Hz), 7.50 (dd, 2 H, J=6.5, 2.0 Hz), 7.99 (dd, 2 H, J=6.5, 2.0 Hz).

Ethyl 4-(4-(6-Benzyloxyimino-2-methylcyclohex-1-enyl)but-3-en-1-ynyl)-3-eneynyl)benzoate
(Compound 11)

Ethyl 4-(4-(2-Methyl-6-oxocyclohexen-1-yl)but-3-en-1-ynyl)benzoate (Compound F, 80 mg, 0.26 mmol) was dissolved in ethanol (8 mL) and treated with benzyloxylamine hydrochloride (413 mg, 2.6 mmol) and sodium acetate trihydrate (529 mg, 3.9 mmol). The resulting solution was degassed with argon, protected from light, and stirred for 20 hours at room temperature. The solution was concentrated in vacuo, diluted with saturated ammonium chloride, and the products were extracted 3 times with ethyl ether. The combined organic layers were washed with water, and brine, dried (MgSO$_4$), filtered, and the solvents were removed in vacuo to give a yellow oily solid as a residue. The residue was purified by silica gel chromatography using a solution of hexane and ethyl acetate in a 95 to 5 ratio, respectively, to give the title compound as a yellow solid.

PNMR (300 MHz, CDCl$_3$) δ 1.40 (t, 3 H, J=7.2 Hz), 1.69 (m, 2 H, J=6.2 Hz), 2.00 (s, 3 H), 2.24 (t, 2 H, J=6.1 Hz), 2.64 (t, 2 H, J=6.5 Hz), 4.38 (q, 2 H, J=7.2 Hz), 5.15 (s, 2 H), 6.28 (d, 1 H, J=16 Hz), 6.95 (d, 1 H, J=16 Hz), 7.26–7.45 (m, 5 H), 7.51 (d, 2 H, J=8.6 Hz), 7.99 (dd, 2 H, J=6.7, 2.0 Hz).

Ethyl 4-(4-(6-Ethoxycarbonylmethylene-2-methylcyclohex-1-enyl)but-3-en-1-ynyl)benzoate
(Compound 12)

A solution of ethyl 4-(4-(2-methyl-6-oxocyclohexen-1-yl) but-3-en-1-ynyl)benzoate (Compound F, 500 mg, 1.62 mmol), zinc powder (2.0 g, 31 mmol), ethyl bromoacetate (0.36 mL, 3.24 mmol) and anhydrous benzene (8 mL) was refluxed under argon for 2 hours. The solution was cooled to room temperature and filtered through Celite. The filtrate was diluted with ethyl acetate and washed with saturated ammonium chloride, water, brine, dried (MgSO$_4$), and filtered, and the solvents were removed in vacuo to give a yellow oily solid as a residue. The residue was purified by silica gel chromatography using a solution of hexane and ethyl acetate in a 90 to 10 ratio, respectively, to give the desired tertiary alcohol. This alcohol was dissolved in toluene (20 mL), treated with Burgess Reagent (CH$_3$O$_2$CNSO$_2$N(C$_2$H$_5$)$_3$) (1.58 g, 6.62 mmol) and stirred at 50° C. for 1 hour. The resulting solution was cooled to room temperature, diluted with ethyl acetate and washed with saturated ammonium chloride, water, and brine, and dried (MGSO4). The organic phase was concentrated under reduced pressure and the residue partially purified by silica gel chromatography (ethyl acetate:hexane::7:93). The title compound was obtained from the resulting mixture of three compounds by reverse phase HPLC using 20% water in acetonitrile on a standard column.

PNMR (300 MHz, CDCl$_3$) δ 1.29 (t, 3 H, J=7.1 Hz), 1.40 (t, 3 H, J=7.1 Hz), 1.75 (m, 2 H, J=6.5 Hz), 1.94 (s, 3 H), 2.27 (t, 2 H, J=6.1 Hz), 2.99 (t, 2 H J=6.3 Hz), 4.15 (q, 2 H, J=7.1 Hz), 4.38 (q, 2 H, J=7.1 Hz), 5.74 (s, 1 H), 5.77 (d, 1 H, J=16 Hz), 6.68 (d, 1 H, J=16 Hz), 7.51 (dd, 2 H, J=6.6, 1.7 Hz), 8.00 (dd, 2 H, J=6.6, 1.9 Hz)

What is claimed is:

1. A compound having the structure in accordance with a formula selected from the group consisting to formulas 1, 2, 3 and 4,

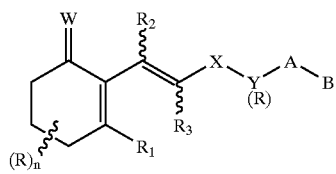
Formula 1

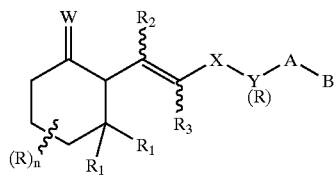
Formula 2

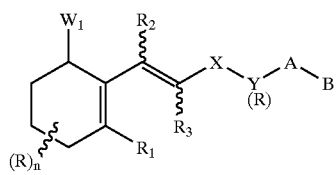
Formula 3

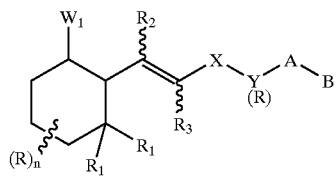
Formula 4 wherein R, $R_1$, $R_2$ and $R_3$ are H, lower alkyl of 1 to 10 carbons, cycloalkyl of 3 to 10 carbons, halogen, ($C_{1-10}$-lower alkyl)$_3$-silyl, $C_{1-10}$-lower alkylphenyl, or phenyl-$C_{1-10}$-lower alkyl, n is an integer having the values of 0 to 6;

W is O, S, C(R)$_2$, CRCO$_2$R, NR, NOR, NN(R)$_2$;

W$_1$ is OR, SR, N(R)$_2$, RC(O)O, RC(S)O, RC(O)S, NRC(O)R, NRC(S)R, NRC(O)N(R)$_2$, NRC(S)N(R)$_2$, OC(O)OR, and SC(O)OR;

X is C≡C, C(O)O, C(O)S, CONR, CSNR, and (CR=CR)$_{n'}$ where n' is an integer having the values 1 to 5;

Y is heteroaryl selected from a group consisting of pyridyl, thienyl, furyl, pyridazinyl, pyrimidinyl, pyrazinyl, thiazolyl, oxazolyl, imidazolyl and pyrrazolyl, said heteroaryl group being optionally substituted with one or two R groups;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, or tri-lower alkylsilyl, where R$_7$ is an alkyl, cycloalkyl or alkenyl group containing 1 to 5 carbons, R$_8$ is an alkyl group of 1 to 10 carbons or (trimethylsilyl)alkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alky, and R$_{13}$ is divalent alkyl radical of 2–5 carbons, or a pharmaceutically acceptable salt of said compound.

2. A compound in accordance with claim 1 having the structure of Formula 1.

3. A compound in accordance with claim 1 having the structure of Formula 2.

4. A compound in accordance with claim 1 having the structure of Formnula 3.

5. A compound in accordance with claim 1 having the structure of Formula 4.

6. A compound in accordance with claim 1 wherein X is —C≡C—.

7. A compound in accordance with claim 1 wherein Y is a bivalent thienyl, furyl or pyridyl group.

8. A compound having the structure in accordance with a formula selected from the group consisting of formulas 1, 2, 3 and 4,

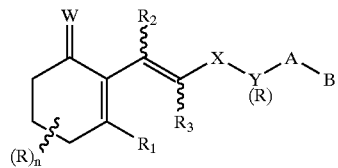
Formula 1

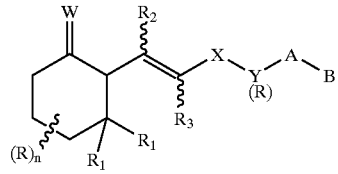
Formula 2

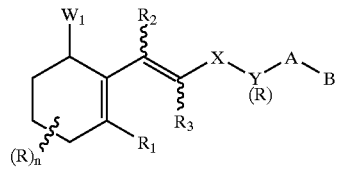
Formula 3

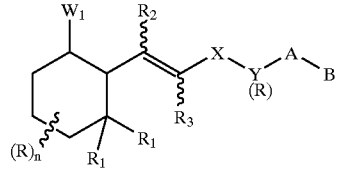
Formula 4 wherein R, $R_1$, $R_2$ and $R_3$ are H, lower alkyl of 1 to 10 carbons, cycloalkyl of 3 to 10 carbons, halogen, ($C_{1-10}$-loweralkyl)$_3$-silyl, $C_{1-10}$-lower alkylphenyl, or phenyl-$C_{1-10}$-lower alkyl, n is an integer having the values of 0 to 6;

W is O, S, C(R)$_2$, CRCO$_2$R, NR, NOR, NN(R)$_2$;

W$_1$ is OR, SR, N(R)$_2$, RC(O)O, RC(S)O, RC(O)S, NRC(O)R, NRC(S)R, NRC(O)N(R)$_2$, NRC(S)N(R)$_2$, OC(O)OR, and SC(O)OR;

X is C(O)S, CONR, or CSNR;

Y is a phenyl or naphthyl group, or heteroaryl selected from a group consisting of pyridyl, thienyl, furyl, pyridazinyl, pyrimidinyl, pyrazinyl, thiazolyl, oxazolyl, imidazolyl and pyrrazolyl, said phenyl, naphthyl and heteroaryl groups being optionally substituted with one or two R groups;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, or tri-lower alkylsilyl, where R$_7$ is an alkyl, cycloalkyl or alkenyl group containing 1 to 5 carbons, R$_8$ is an alkyl group of 1 to 10 carbons or (trimethylsilyl)alkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons, or a pharmaceutically acceptable salt of said compound.

9. A compound having the structure in accordance with a formula selected from the group consisting of formulas 3 and 4,

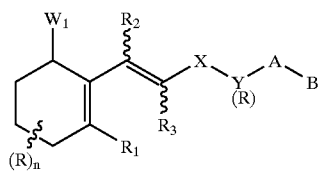

Formula 3

-continued

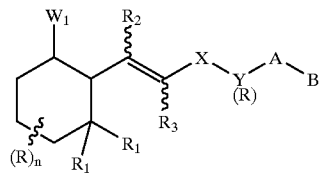

Formula 4 wherein R, R$_1$, R$_2$ and R$_3$ are H, lower alkyl of 1 to 10 carbons, cycloalkyl of 3 to 10 carbons, halogen, (C$_{1-10}$-lower alkyl)$_3$-silyl, C$_{1-10}$-lower alkylphenyl, or phenyl-C$_{1-10}$-lower alkyl, n is an integer having the values of 0 to 6;

W$_1$ is RC(S)O, RC(O)S, OC(O)OR or SC(O)OR;

X is C≡C, C(O)O, C(O)S, CONR, CSNR, and (CR=CR)$_{n'}$ where n' is an integer having the values 1 to 5;

Y is a phenyl or naphthyl group said phenyl or naphthyl groups being optionally substituted with one or two R groups;, or when X is —(CR=CR)$_{n'}$—and n' is 3, 4 or 5 then Y represents a direct valence bond between said (CR=CR)$_{n'}$ group and B;

A is (CH$_2$)$_q$ where q is 0–5, lower branched chain alkyl having 3–6 carbons, cycloalkyl having 3–6 carbons, alkenyl having 2–6 carbons and 1 or 2 double bonds, alkynyl having 2–6 carbons and 1 or 2 triple bonds;

B is hydrogen, COOH or a pharmaceutically acceptable salt thereof, COOR$_8$, CONR$_9$R$_{10}$, —CH$_2$OH, CH$_2$OR$_{11}$, CH$_2$OCOR$_{11}$, CHO, CH(OR$_{12}$)$_2$, CHOR$_{13}$O, —COR$_7$, CR$_7$(OR$_{12}$)$_2$, CR$_7$OR$_{13}$O, or tri-lower alkylsilyl, where R$_7$ is an alkyl, cycloalkyl or alkenyl group containing 1 to 5 carbons, R$_8$ is an alkyl group of 1 to 10 carbons or (trimethylsilyl)alkyl where the alkyl group has 1 to 10 carbons, or a cycloalkyl group of 5 to 10 carbons, or R$_8$ is phenyl or lower alkylphenyl, R$_9$ and R$_{10}$ independently are hydrogen, an alkyl group of 1 to 10 carbons, or a cycloalkyl group of 5–10 carbons, or phenyl or lower alkylphenyl, R$_{11}$ is lower alkyl, phenyl or lower alkylphenyl, R$_{12}$ is lower alkyl, and R$_{13}$ is divalent alkyl radical of 2–5 carbons, or a pharmaceutically acceptable salt of said compound.

* * * * *

UNITED STATES PATENT AND TRADEMARK OFFICE
CERTIFICATE OF CORRECTION

PATENT NO. : 6,465,647 B1
DATED : October 15, 2002
INVENTOR(S) : Beard et al.

It is certified that error appears in the above-identified patent and that said Letters Patent is hereby corrected as shown below:

Column 1,
Line 37, "a topic" should be -- atopic --.

Column 2,
Line 16, "refinoid" should be -- retinoid --.

Column 3,
Line 66, "(CR≡CR)$_n$." should be -- (CR=CR)$_{n'}$ --.

Column 4,
Line 38, "a topic derrnatitis" should be -- atopic dermatitis --.

Column 6,
Line 22, "PAR$_\alpha$" should be -- RAR$_\alpha$ --.

Column 7,
Line 49, "ofthe" should be -- of the --.
Line 66, "oinithine" should be -- ornithine --.

Column 8,
Line 64, "usefuil" should be -- useful --.

Column 12,
Line 41, "fonnula" should be -- formula --.

Column 17,
Line 26, Reaction Scheme 3, Formula 13,

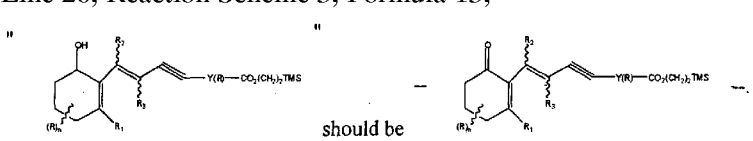

Column 19,
Line 23, "sp" should be -- sp$^3$ --.

Column 21,
Line 40, Reaction Scheme 6, Formula 24,

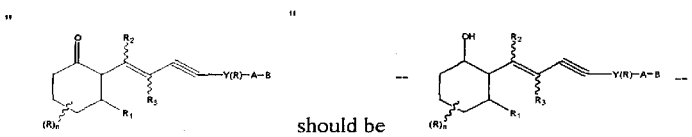

UNITED STATES PATENT AND TRADEMARK OFFICE
CERTIFICATE OF CORRECTION

PATENT NO.   : 6,465,647 B1
DATED        : October 15, 2002
INVENTOR(S)  : Beard et al.

It is certified that error appears in the above-identified patent and that said Letters Patent is hereby corrected as shown below:

Column 27,
Line 46, "2-(2-4 iodoethenyl" should be -- 2-(2-iodoethenyl --.

Column 28,
Line 35, Reaction Scheme 9,

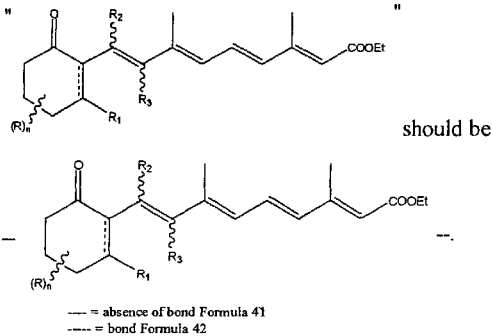

Line 55, "[5-3" should be -- [5- --.

Column 29,
Line 54, Reaction Scheme 10, Formula 43/44,

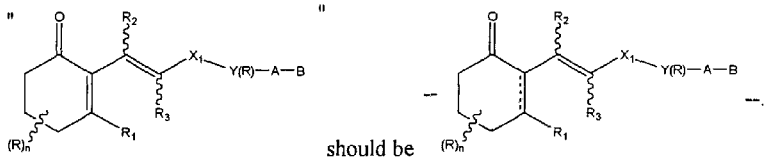

Column 30,
Line 61, "sti rre d" should be -- stirred --.

Column 31,
Line 44, "(+)" should be -- (±) --.

Column 33,
Line 7, "Hz," should be -- Hz), --.
Line 36, "methyicyclohex" should be -- methylcyclohex --.
Line 53, "-E-" should be -- -(E)- --.

UNITED STATES PATENT AND TRADEMARK OFFICE
CERTIFICATE OF CORRECTION

PATENT NO.    : 6,465,647 B1
DATED         : October 15, 2002
INVENTOR(S)   : Beard et al.

It is certified that error appears in the above-identified patent and that said Letters Patent is hereby corrected as shown below:

Column 34,
Line 56, "(+)" should be -- (±) --.

Signed and Sealed this

Second Day of September, 2003

JAMES E. ROGAN
*Director of the United States Patent and Trademark Office*